United States Patent
Bu et al.

(10) Patent No.: US 11,220,703 B2
(45) Date of Patent: Jan. 11, 2022

(54) FLUOROMETRIC AND COLORIMETRIC QUANTIFICATION TECHNIQUES WITH AUTONOMOUSLY AND REVERSIBLY STALLING CATALYTIC SIGNAL AMPLIFICATION

(71) Applicants: University of Pittsburgh - Of the Commonwealth System of Higher Education, Pittsburgh, PA (US); Merck Sharp & Dohme Corp., Rahway, NJ (US)

(72) Inventors: Xiaodong Bu, Kenilworth, NJ (US); Junyong Jo, Kenilworth, NJ (US); Kazunori Koide, Pittsburgh, PA (US); Matthew Patrick Tracey, Pittsburgh, PA (US); Christopher J. Welch, Kenilworth, NJ (US)

(73) Assignees: University of Pittsburgh—Of the Commonwealth System of Higher Education, Pittsburgh, PA (US); Merck Sharp & Dohme Corp., Rahway, NJ (US)

( * ) Notice: Subject to any disclaimer, the term of this patent is extended or adjusted under 35 U.S.C. 154(b) by 181 days.

(21) Appl. No.: 15/778,855

(22) PCT Filed: Nov. 23, 2016

(86) PCT No.: PCT/US2016/063611
§ 371 (c)(1),
(2) Date: May 24, 2018

(87) PCT Pub. No.: WO2017/091733
PCT Pub. Date: Jun. 1, 2017

(65) Prior Publication Data
US 2018/0355401 A1 Dec. 13, 2018

Related U.S. Application Data

(60) Provisional application No. 62/259,258, filed on Nov. 24, 2015.

(51) Int. Cl.
*C12Q 1/28* (2006.01)
*G01N 33/53* (2006.01)
*C12N 9/02* (2006.01)

(52) U.S. Cl.
CPC ............ *C12Q 1/28* (2013.01); *C12N 9/0004* (2013.01); *G01N 33/5308* (2013.01); *G01N 2333/90245* (2013.01)

(58) Field of Classification Search
CPC .................. C12N 9/0004; C12Q 1/28; G01N 2333/90245; G01N 33/5308
See application file for complete search history.

(56) References Cited

U.S. PATENT DOCUMENTS

| | | | | |
|---|---|---|---|---|
| 4,960,693 | A | * 10/1990 | Siddiqi | G01N 33/542 435/15 |
| 5,512,451 | A | * 4/1996 | Kricka | C12Q 1/28 435/28 |
| 5,629,168 | A | 5/1997 | Kricka | |
| 2003/0224476 | A1* | 12/2003 | Chou | A61K 39/0007 435/68.1 |
| 2014/0220612 | A1 | 8/2014 | Batchelor et al. | |

OTHER PUBLICATIONS

Reinen et al. J. Biomolec. Screening (2011) 16(2): 239-250 (Year: 2011).*
Registry file entry for 1357085-84-7 from STN. downloaded Dec. 5, 2019 (Year: 2019).*
Navas Diaz et al. Analytica Chimica Acta (1996) 327: 161-165 (Year: 1996).*
Kam et al. Bioconjugate Chem. (1993) 4: 560-567 (Year: 1993).*
Ugarova et al. Biochim. Biophys. Acta (1987) 921(3): 465-472 (Year: 1987).*
Zhu et al. Tetrahedron (2004) 60: 7267-7275 (Year: 2004).*
Garner et al. J. Am. Chem. Soc. (2009) 131: 5163-5171 (Year: 2009).*
Bu et al., "Rapid Analysis of Residual Palladium in Pharmaceutical Development Using a Catalysis-Based Fluorometric Method", Organic Process Research & Development, 2012, pp. 108-113, vol. 17.
Bullock et al., "Optimization and Scale-Up of a Suzuki-Miyaura Coupling Reaction: Development of an Efficient Palladium Removal Technique", Organic Process Research & Development, 2008, pp. 896-899, vol. 12.
Carter et al., "Fluorescent Sensors for Measuring Metal Ions in Living Systems", Chemical Reviews, 2014, pp. 4564-4601, vol. 114.
Cui et al., "A novel ratiometric sensor for the fast detection of palladium species with large red-shift and high resolution both in aqueous solution and solid state", Analytica Chimica Acta, 2013, pp. 139-145, vol. 786.
Demontellano et al., "Mechanism-Based Inactivation of Horseradish Peroxidase by Sodium Azide. Formation of meso-Azidoprotoporphyrin IX", Biochemistry, 1988, pp. 5470-5476, vol. 27.
Engvall et al., "Enzyme-Linked Immunosorbent Assay. II. Quantitative Assay of Protein Antigen, Immunoglobulin G, By Means of Enzyme-Labelled Antigen and Antibody-Coated Tubes", Biochimica et Biophysica Acta, 1971, pp. 427-434, vol. 251.
Garner et al., "Enhancement of a Catalysis-Based Fluorometric Detection Method for Palladium through Rational Fine-Tuning of the Palladium Species", J. Am. Chem. Soc., 2009, pp. 5163-5171, vol. 131.
Goldberg et al., "Methods for measurement of antibody/antigen affinity based on ELISA and RIA", Current Opinion in Immunology, 1993, pp. 278-281, vol. 5.
Hettie et al., "Selective Catecholamine Recognition with NeuroSensor 521: A Fluorescent Sensor for the Visualization of Norepinephrine in Fixed and Live Cells", ACS Chemical Neuroscience, 2013, pp. 918-923, vol. 4.

(Continued)

*Primary Examiner* — Susan M Hanley
(74) *Attorney, Agent, or Firm* — The Webb Law Firm

(57) ABSTRACT

Provided herein are analytical methods utilizing a self-limiting catalytic reaction, and compositions and kits useful therefore. In one aspect the method is used to quantify Pd, and in another, the method is a horseradish peroxidase assay.

16 Claims, 18 Drawing Sheets

(56) References Cited

OTHER PUBLICATIONS

Huang et al., "Horseradish peroxidase-catalyzed synthesis of poly(thiophene-3-boronic acid) biocomposites for mono-/bi-enzyme immobilization and amperometric biosensing", Biosensors and Bioelectronics, 2013, pp. 41-47, vol. 44.

Koide et al., "A competitive and reversible deactivation approach to catalysis-based quantitative assays", Nature Communications, 2016, p. 1-7, vol. 7, No. 10691.

Konnick et al., "Reaction of Molecular Oxygen with a Pdll-Hydride To Produce a Pdll-Hydroperoxide: Experimental Evidence for an HX-Reductive-Elimination Pathway", J. Am. Chem. Soc., 2008, pp. 5753-5762, vol. 130.

Kuroda et al., "New phenylboronic acid derivatives as enhancers of the luminol-H2O2-horseradish peroxidase chemiluminescence reaction", Luminescence, 1999, pp. 361-364, vol. 14.

Li et al., "Optical Pd2+ sensing by rhodamine hydrazone ligands: different stoichiometries in aqueous/nonaqueous environments", Tetrahedron Letters, 2013 pp. 4357-4361, vol. 54.

Liu et al., "Water-Soluble Colorimetric and Ratiometric Fluorescent Probe for Selective Imaging of Palladium Species in Living Cells", Inorganic Chemistry, 2014, pp. 12590-12594, vol. 53.

Namiki et al., "Optical glutamate sensor for spatiotemporal analysis of synaptic transmission", European Journal of Neuroscience, 2007, pp. 2249-2259, vol. 25.

Ren et al. "Rapid responsive palladium sensor under mild condition", Sensors and Actuators B: Chemical, 2012, pp. 1277-1282, vols. 171-172.

Song et al., "A Highly Sensitive Fluorescent Sensor for Palladium Based on the Allylic Oxidative Insertion Mechanism", J. Am. Chem. Soc, 2007, pp. 12354-12355, vol. 129.

Song et al., "Studies Toward an Ideal Fluorescence Method to Measure Palladium in Functionalized Organic Molecules: Effects of Sodium Borohydride, Temperature, Phosphine Ligand, and Phosphate Ions on Kinetics", Chem. Eur. J, 2010, pp. 13500-13508, vol. 16.

Thayer, "Trace Metals Debate", Chemical & Engineering News, 2013, pp. 10-13, vol. 91., No. 33.

Wang et al., "Screening Binary Systems of Chelating Agents Combined with Carbon or Silica Gel Adsorbents: The Development of a Cost-Effective Method to Remove Palladium from Pharmaceutical Intermediates and APIs", Org. Process Res. Dev., 2011, pp. 1371-1376, vol. 15.

Welch et al., "Adsorbent Screening for Metal Impurity Removal in Pharmaceutical Process Research", Organic Process Research & Development, 2005, pp. 198-205, vol. 9, No. 2.

Williams et al., "A High-Throughput Method To Detect Palladium in Ores", Ind. Eng. Chem. Res., 2013, pp. 8612-3615, vol. 52.

Yang et al., "A novel selective fluorescent and colorimetric chemosensor for the visual detection of Pd2+ and application of imaging in living cells", Inorganic Chemistry Communications, 2014, pp. 310-314, vol. 46.

Zhang et al., "Fluorescent Detection of Chemical Warfare Agents: Functional Group Specific Ratiometric Chemosensors", J. Am Chem. Soc , 2003, pp. 3420-3421, vol. 125.

* cited by examiner

| | P1 | P2 | P3 | P4 | P5 | P6 | P7 | P8 | P9 | P10 | P11 | P12 | P13 | P14 | P15 |
|---|---|---|---|---|---|---|---|---|---|---|---|---|---|---|---|
| 0 | 0.8 | 0.8 | 0.8 | 0.8 | 0.8 | 0.8 | 0.8 | 0.8 | 0.8 | 0.8 | 0.8 | 0.8 | 0.8 | 0.8 | 0.8 |
| 25 | 1.1 | 0.4 | 0.8 | 1.6 | 1.2 | 0.9 | 2.5 | 0.9 | 2.3 | 3.6 | 4.5 | 1.0 | 0.7 | 0.9 | 0.6 |
| 50 | 1.3 | 0.4 | 1.8 | 1.2 | 1.3 | 1.0 | 3.1 | 0.7 | 2.3 | 3.4 | 4.4 | 1.3 | 0.7 | 1.1 | 0.8 |
| 100 | 1.3 | 0.5 | 0.5 | 1.4 | 1.3 | 1.1 | 3.4 | 0.9 | 2.5 | 3.4 | 4.4 | 1.0 | 0.8 | 1.0 | 0.7 |
| 200 | 1.1 | 0.2 | 0.6 | 1.1 | 1.5 | 1.2 | 3.6 | 1.2 | 2.5 | 2.8 | 4.8 | 0.9 | 0.9 | 1.0 | 0.7 |
| 400 | 1.0 | 0.2 | 0.6 | 1.2 | 1.5 | 1.2 | 3.4 | 0.7 | 2.2 | 1.7 | 3.8 | 0.9 | 0.7 | 0.9 | 0.5 |

[phosphine] in μM

FLUOROMETRIC AND COLORIMETRIC QUANTIFICATION TECHNIQUES WITH AUTONOMOUSLY AND REVERSIBLY STALLING CATALYTIC SIGNAL AMPLIFICATION

CROSS REFERENCE TO RELATED APPLICATIONS

This application is the U.S. national phase of International Application No. PCT/US2016/063611 filed Nov. 23, 2016, and claims the benefit of U.S. Provisional Patent Application No. 62/259,258, filed Nov. 24, 2015, each of which is incorporated herein by reference in its entirety.

STATEMENT REGARDING FEDERAL FUNDING

This invention was made with the government support under Grant No. CHE0911092 awarded by the National Science Foundation. The government has certain rights to the invention.

Development of optical assays for facile quantification of trace analytes is an ever-expanding field. Target analytes range from trace metals and biological signaling agents to chemical weapons. Tailored chemosensors interact specifically with an analyte to produce an optically decoded signal, which can manifest itself as a wavelength shift or intensity change in either absorbance or emission. These signals are measured by simple instrumentation, such as a plate reader, or visualized with the naked eye.

Quantitative optical assays exploit either a catalytic or a non-catalytic reaction. Non-catalytic assays rely on a single turnover from the analyte for a chemical conversion or a reversible binding and have the benefit of time-independence; in other words, the signal does not change over time once the reaction or binding event is complete. A major drawback of these systems is the higher limits of quantification due to this limited turnover, rendering these non-catalytic assays undesirable for detection of trace analytes. A more sensitive approach for trace analytes employs catalysis-based assays, where the substrate continues to react over time, amplifying signals. The continuity of catalysis-based signal amplification presents some practical challenges to assay development. In metal catalysis-based assays, once the metal has entered into the catalytic cycle, the resulting fluorescence signal is dependent on the concentration of the analyte as well as the time elapsed—with the reaction continuing until the fluorogenic substrate is consumed. In enzyme and enzyme-linked immunosorbent assays (ELISA), the reaction continues until the substrate is consumed or a terminating reagent is added. In either case, if an analyte is abundant, the assay substrate will be rapidly consumed, preventing accurate quantitation. Additionally, if a reaction with a low concentration of analyte is allowed to continue unchecked, the signal can increase to the point where the detector becomes saturated—again preventing accurate quantitation. Finally, when a catalysis-based assay is externally stopped, it cannot be restarted, and premature termination requires that the assay be repeated to obtain quantitative data. As such, a significant drawback associated with catalysis-based assays is the far narrower dynamic range (1-2 orders of magnitude) compared to more labor-intensive methods, such as inductively coupled-plasma mass spectrometry (ICP-MS), which has a detection range up to 5 orders of magnitude. New methodologies that overcome these limitations to enable controlled activity of catalytic assays would be broadly useful in chemical and biochemical research.

In a specific example, analysis of trace palladium routinely uses inductively coupled-plasma mass spectrometry (ICP-MS) or inductively coupled-plasma optical emission spectroscopy (ICP-OES). These methods are sensitive and robust, spanning several orders of magnitude in their dynamic range but the everyday use of these approaches is hindered by expensive instrumentation, low throughput, and lack of availability at the sites in which samples are produced. Optical methods based on catalysis have been developed to quantify palladium in samples including pharmaceuticals; however, the inherent time-dependence for catalysis and narrow linear dynamic ranges for absorption or emission signals render these methods less than ideal.

SUMMARY

The ability of a single analyte molecule to continuously produce multiple signal molecules makes catalysis-based optical assays highly sensitive and widely useful in chemical and biochemical research. However, the continuous signal generation causes the chromogenic or fluorogenic reaction to persist until the substrate is depleted or the catalyst is chemically deactivated. Consequently, catalysis-based assays require 'fine tuning' of conditions to avoid signal saturation, substrate depletion, and nonlinear assay performance. Furthermore, once stopped, such assays cannot be re-started. As such, the dynamic range of optical methods has been limited to 2 orders of magnitude at best with respect to analyte concentrations. Additionally, analytes more abundant than the assay substrate cannot be quantified by a catalysis-based assay due to rapid signal saturation.

According to one aspect of the invention, provided herein is a rapid, colorimetric method for palladium detection, employing the cleavage of an allylic ether from the chemodosimeter, allyl resorufin ether (ARE), to release resorufin, shifting the color of the solution from yellow to purple. Uniquely, the method exhibits an autonomous, reversible stalling under certain conditions, allowing for the reaction to stop after a controlled amount of time. Fine-tuning reaction components allows the reaction to continue for longer periods of time. This new method, through serial additions of $NaBH_4$ to a single solution, can quantify palladium concentrations ranging over 5 orders of magnitude, rivaling ICP-MS and ICP-OES. The deallylation of ARE to form resorufin was tested successfully in residual palladium detection in pharmaceuticals, ores, and organic polymers. The method is colorimetric, allowing for users to visually estimate quantities of palladium in samples without instruments.

According to one aspect of the invention, a method of detecting an analyte in a test sample is provided. The method comprises: (a) conducting a catalytic reaction that produces a detectable product in the presence of an analyte in a reaction mixture in the presence of an inactivator of the reaction, wherein the inactivator depletes a limiting component of the reaction, thereby stalling the reaction; (b) restoring, in the presence of the inactivator, the depleted limiting component to restart the reaction one or more times, wherein the inactivator depletes the restored limiting component of the reaction thereby again stalling the reaction; and (c) detecting the presence of the detectable product of the catalytic reaction in the reaction mixture. In one aspect, the limiting component is a catalyst of the catalytic reaction. In another aspect, the limiting component is a cofactor or substrate of the reaction. In a further aspect, the reaction is catalyzed by an enzyme, and the limiting component is a substrate of the enzyme. In one example, the enzyme is a peroxidase, and the limiting factor is $H_2O_2$. In another, the inactivator is a boronic acid, such as phenylboronic acid. In one aspect, the limiting component is depleted by oxidation and is restored by addition of a reducing agent. In another, the limiting component is depleted by oxidation in the presence of oxygen. In one example, the analyte is Pd, the reaction mixture comprises resorufin allyl ether (RAE) and $NH_4OAc$ in ethanol, and the restorative composition comprises $NaBH_4$, and the reaction is conducted under an oxygen-containing environment, such as under oxygen, an oxygen-containing gas mixture, or air. In one aspect, the reaction is conducted in a multi-well plate, with at least two wells optionally comprising different amounts of $NaBH_4$. In one aspect, the reaction is a HRP-detection reaction, the limiting component is $H_2O_2$, the inactivator is $PhB(OH)_2$, and the restorative composition comprises $H_2O_2$.

In another aspect, a compound having the structure:

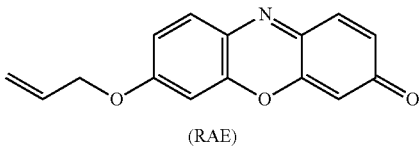 [SMILES: C=CCOc1ccc2nc3ccc(=O)cc-3oc2c1]

(RAE)

is provided. In another aspect a composition comprising resorufin allyl ether (RAE) is provided. In yet another aspect, a composition comprising ethanol, resorufin allyl ether (RAE), and $NH_4OAc$, optionally Pd, and optionally $NaBH_4$ is provided. In another aspect, a composition comprising horseradish peroxidase, $H_2O_2$, and a boronic acid, such as phenylboronic acid is provided.

In another aspect of the invention, an array is provided, comprising at more than one discrete, addressable locations, a composition comprising resorufin allyl ether (RAE), and optionally ethanol, Pd, $NH_4OAc$, and/or $NaBH_4$, and optionally wherein the $NaBH_4$ is in different amounts in at least two different locations of the array. A kit also is provided comprising one or more vessels containing resorufin allyl ether (RAE) and optionally $NH_4OAc$, ethanol, individually or within the same vessel and a vessel comprising $NaBH_4$. In none aspect, the kit comprises a cartridge comprising the vessels, wherein the kit optionally is a cartridge, such as a disposable cartridge, for use in an automated system.

In another aspect, an array is provided, comprising at more than one discrete, addressable locations, a peroxidase, such as a horseradish peroxidase (HRP), $H_2O_2$, a colorimetric substrate for the peroxidase, such as Amplex Red, and a boronic acid, such as $PhB(OH)_2$, and optionally wherein the $H_2O_2$ is present in different amounts at different locations of the array. In another aspect, a kit is provided comprising one or more vessels containing a peroxidase, such as HRP, $H_2O_2$, a colorimetric substrate for the peroxidase, such as Amplex Red, and $PhB(OH)_2$, individually or within the same vessel and a vessel comprising $H_2O_2$. The kit optionally comprises a cartridge comprising the vessels, such as a disposable cartridge, for use in an automated system.

BRIEF DESCRIPTION OF THE DRAWINGS

FIG. 1, panel (a) shows widely used catalytic assays continuously convert a substrate to a reporter molecule. FIG. 1, panel (b) shows that this work presents an autonomously stop-and-go paradigm, in which there is a competition between the catalytic reaction and autonomous deactivation of the catalyst (linked to analyte concentration) or the essential reagent. Addition of an activator or a reactant restores the system.

FIG. 9A shows metal selectivity of RAE deallylation measured under the following conditions: 29 μM RAE, 100 μM metal except $Pd^{2+}$ at 10 μM, 3 mM $NaBH_4$, 200 μM TFP, 800 mM $NH_4OAc$, EtOH, 24° C., 60 min. n=3. Higher absorbance of Ag, Hg, and Au samples was due to opacity. The photograph was taken under ambient light. FIG. 9B shows fluorescence intensities vs. metal of the reaction solutions from (FIG. 9A). FIG. 9C shows metal selectivity with mixture of Pd and other metals in a 1:10 ratio. 29 μM RAE, 100 μM metal, 10 μM Pd2+, 3 mM $NaBH_4$, 200 μM TFP, 800 mM $NH_4OAc$, EtOH, 24° C., 60 min. n=3.

FIG. 17A shows structures of previously developed fluorogenic chemodosimeter APE and its conversion to Pittsburgh Green. FIG. 17B shows chromogenic chemodosimeter RAE and its conversion to resorufin. FIG. 17C shows absorption spectra of resorufin and RAE in 800 mM NH$_4$OAc in EtOH. The data are normalized to 20 μM of each compound.

FIG. 18A shows reaction lifetime dictated by NaBH$_4$ concentration. Conditions: 29 μM RAE, 10 ppb Pd(II), 200 μM TFP, 800 mM NH$_4$OAc, 0-125 mM NaBH$_4$, EtOH, 25° C. FIG. 18B shows stalled deallylation reaction can be restarted by NaBH$_4$ addition. Conditions: 29 μM RAE, 0.3 ppm Pd$^{2+}$, 200 μM TFP, 800 mM NH$_4$OAc, 0. 0.6, 1.2, 1.8, 2.4 mM NaBH$_4$, added as 2.5 M aliquots at indicated time points. FIG. 18C shows various NH$_4$OAc concentrations do not have an effect on reaction lifetime. Conditions: 29 μM RAE, 0.3 ppm Pd$^{2+}$, 200 μM TFP, 0-800 mM NH$_4$OAc, 0.6 mM NaBH$_4$. Samples were basified with 1 N NaOH prior to fluorescence reading.

FIG. 19A shows the appearance of distinguishable color correlating to Pd concentration occurs in less than one minute using a set of palladium standards. Conditions: 29 μM RAE, 0-4.0 ppm Pd, 200 μM TFP, 800 mM NH$_4$OAc, 1.0 mM NaBH$_4$, EtOH, 25° C. FIG. 19B is colorimetric plate showing dependence of color formation on Pd and NaBH$_4$ concentration. 29 μM RAE, 200 μM TFP, 0-50 ppm Pd, 0-100 mM NaBH$_4$, 800 mM NH$_4$OAc 25° C., EtOH, 10 min, n=3. FIG. 19C shows the conditions: Colorimetric analysis as reported in FIG. 19A; ICP-MS analysis as reported in "Materials and Methods" section of Examples 2 and 3.

FIG. 20, panel (a) shows screening kits containing 48 commercial adsorbents (L. Wang et al., Screening binary systems of chelating agents combined with carbon or silica gel adsorbents: The development of a cost-effective method to remove palladium from pharmaceutical intermediates and APIs. *Org. Process Res. Dev.* 15, 1371-1376 (2011)) are exposed to a solution of the Pd-containing intermediate. FIG. 20, panel (b) are aliquots from screening kits, which are evaluated for Pd content using the colorimetric method, as described in protocol. FIG. 20, panel (c)—Finding the best potential hits visually by adding more NaBH$_4$. FIG. 20, panel (d) is high-throughput mapping of relative Pd concentration by measurement of UV-Vis 570 nm/460 nm using UV-Vis plate reader.

FIG. 21A shows conversion of Amplex Red to resorufin. FIG. 21B shows the effect of PhB(OH)$_2$ (phenylboronic acid) on horseradish peroxidase assay. Conditions: 50 μM Amplex Red, 0.1 U/mL horseradish peroxidase, 25 μM H$_2$O$_2$, 0, 25, 50, 250 mM PhB(OH)$_2$, PBS pH 7.4. A stock solution of H$_2$O$_2$ was added to solution containing PBS or PBS containing PhB(OH)$_2$ and allowed to react for 10 min prior to addition to Amplex Red and horseradish peroxidase. FIG. 21C shows restarting a stopped enzymatic reaction in the presence of an inhibitor. Conditions: 50 μM Amplex Red, 0.05 U/mL horseradish peroxidase, 0 μM H$_2$O$_2$ (0-20 min) for the black circle and dark red triangle. For others 10 μM H$_2$O$_2$ at 0 min, 20 μM H$_2$O$_2$ at 10 min, 0 or 5 mM PhB(OH)$_2$, PBS pH 7.4. A stock solution of H$_2$O$_2$ was added to solution containing PBS or PBS containing PhB(OH)$_2$ and was allowed to react for 1 min prior to addition to Amplex Red and horseradish peroxidase. FIG. 21D shows restarting a stopped enzymatic reaction in presence of an inhibitor with uninhibited saturation. Conditions; 50 μM Amplex Red, 1 U/mL horseradish peroxidase, 0 μM H$_2$O$_2$ (0-20 min) for the black circle and dark red triangle. For others, 10 μM H$_2$O$_2$ at 0 min, 30 μM H$_2$O$_2$ at 10 min, 0 or 10 mM PhB(OH)$_2$, PBS pH 7.4. A stock solution of H$_2$O$_2$ was added to solution containing PBS or PBS containing PhB(OH)$_2$ and was allowed to react for 1 min prior to addition to Amplex Red and horseradish peroxidase. After the addition of H$_2$O$_2$ at 10 min, the PhB(OH)$_2$-free sample showed a signal above the upper limit of the instrument (above 2,000,000 units).

DETAILED DESCRIPTION

Figure 1:
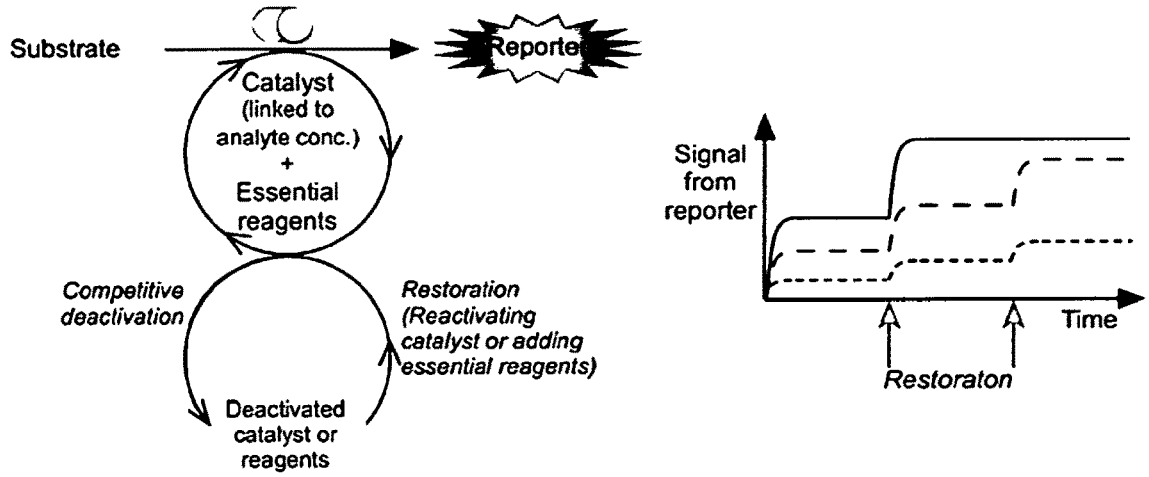
FIG. 1: Continuous reaction and competitively and reversibly deactivated reaction.

Other than in the operating examples, or where otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical values, however, inherently contain certain errors necessarily resulting from the standard deviation found in their respective testing measurements. Furthermore, when numerical ranges of varying scope are set forth herein, it is contemplated that any combination of these values inclusive of the recited values may be used.

Also, it should be understood that any numerical range recited herein is intended to include all sub-ranges subsumed therein. For example, a range of "1 to 10" is intended to include all sub-ranges between and including the recited minimum value of 1 and the recited maximum value of 10, that is, having a minimum value equal to or greater than 1 and a maximum value of equal to or less than 10.

For definitions provided herein, those definitions refer to word forms, cognates and grammatical variants of those words or phrases.

As indicated above, significant drawbacks are associated with current catalysis-based assays, including a far narrower dynamic range (1-2 orders of magnitude) as compared to more labor-intensive methods, such as ICP-MS, which has a detection range of up to 5 orders of magnitude. Described herein is a novel approach that alleviates these unsolved problems, allowing convenient generation of signal over a wide dynamic range. In this approach, a color-forming catalytic reaction takes place in parallel with a competing reaction that either inactivates the catalyst or consumes a limiting reagent required for signal generation. Under these conditions, signal generation proceeds for a limited time, then autonomously stalls, but can be chemically restarted. In a specific example involving a new catalysis-based colorimetric method for palladium (Pd), multiple cycles of reaction stalling and restarting allows accurate measurement with a detection range of over 5 orders of magnitude, including palladium levels significantly above the substrate concentration. This tactical stop-and-restart approach was also extended to a widely-used horseradish peroxidase (HRP) assay, which, in the presence of an $H_2O_2$ scavenger, was autonomously stalled and could be restarted by re-addition of $H_2O_2$. This study indicates that the dynamic range of catalysis-based assays can be significantly broadened by employing competitive and reversible deactivation.

FIG. 1 shows the new approach to catalysis-based assays described herein, in which a catalytic chromogenic reaction competes with the deactivation of the catalyst or depletion of an essential reagent that is required for the reaction to continue. Under these conditions, a signal-producing reaction proceeds for a limited time, then autonomously stalls, but can be reactivated by reagent addition, generating a graph reminiscent of a staircase function in mathematics, as shown in FIG. 1. This approach is exemplified by both a new colorimetric method for quantifying palladium and a horseradish peroxidase assay system. In the analysis of palladium, multiple cycles of reaction stalling and restarting allow accurate measurement with a detection range of over 5 orders of magnitude. Moreover, analyte levels significantly above the substrate concentration can be quantified.

Therefore, provided herein is a method of detecting an analyte in a test sample (see, for example, FIG. 1). The method comprises: a) conducting a catalytic reaction that produces a detectable product in the presence of an analyte in a reaction mixture in the presence of an inactivator of the reaction, wherein the inactivator depletes a limiting component of the reaction, thereby stalling the reaction; b) restoring, in the presence of the inactivator, the depleted limiting component to restart the reaction one or more times, wherein the inactivator depletes the restored limiting component of the reaction thereby again stalling the reaction; and c) detecting the presence of the detectable product of the catalytic reaction in the reaction mixture.

An analyte is any substance an assay is able to identify or quantify. In one aspect, an analyte is a chemical compound or element. As an example, the analyte can be a catalyst for the assay, such as Pd, as illustrated below. In another aspect, the analyte is a substance detected by a binding event between the substance and a binding reagent such as an antibody or an antibody fragment, such as a scFv fragment. An example of such a binding event is the binding of an analyte to an antibody in an immunoassay, such as an enzyme-linked immunosorbent assay (ELISA). A further example of a binding event in an immunoassay is the binding of an antibody to a cellular or tissue target in an immunohistochemical assay. In another aspect, the analyte is a nucleic acid, such as a deoxyribonucleic acid or a ribonucleic acid, and the assay is an in situ hybridization assay, that can be colorimetric, and optionally fluorescent (e.g. FISH, fluorescent in situ hybridization).

The assay is a catalytic assay that uses a catalyst to amplify a signal. A catalyst is a substance that increases the rate of a chemical reaction without itself undergoing any permanent chemical change. As illustrated in the examples herein, catalysts can be a metal, or other compound or composition, or can be an enzyme. One example of a catalyst is Pd(0), and another is horseradish peroxidase.

The catalytic reaction is conducted in the presence of an inactivator of the assay that reversibly inactivates or removes an essential component (reagent) of the catalytic reaction, thereby stalling the catalytic reaction. In one aspect, the reaction stalls before the reaction reaches 100% of detectable product or signal production when the reaction is conducted under the same conditions, but in the absence of the inactivator, and in various aspects, the reaction stalls before it reaches 99%, 95%, 90%, 80%, 75%, 70%, 60%, 50%, 40%, 30%, 25%, 20%, 10%, or 5% of detectable product or signal production when the reaction is conducted under the same conditions, but in the absence of the inactivator. The inactivator can act on any reagent of the catalytic reaction, depleting the catalyst, depleting a cofactor required for activity of the catalyst, or depleting a substrate of the catalytic reaction. A reagent used in an assay that, when depleted, results in the reaction stalling is referred to herein as a "limiting component of the reaction". By "depleting," it is meant physically altering the catalyst, substrate, or cofactor so that it no longer is active in the reaction, for example by chemical modification, or by reducing the activity of the catalyst, substrate, or cofactor, for example by removing an enzyme co-factor, or another associated reagent, that permits the reaction to proceed. In one example, the inactivator stalls the reaction by reversibly-inactivating the catalyst. This may be accomplished, for example and without limitation, by oxidizing or reducing the catalyst, for instance where the catalyst is a metal that is inactivated by oxidation, as exemplified by oxidation of Pd(0) to Pd(2+), below, and optionally where the analyte is the catalyst. In one example, the catalyst is inactivated by oxidizing the catalyst, for example by oxidizing the catalyst in the presence of an oxygen-containing atmosphere. In another example, a substrate of the reaction is depleted, for example by chemical conversion. This is exemplified by the depletion of $H_2O_2$ by a boronic acid, such as $PhB(OH)_2$. A boronic acid has the formula $R-B(OH)_2$, where R is, for example, a $C_1$-$C_{10}$ hydrocarbon, optionally substituted with one to three heteroatoms, such as O, N, and/or S, such as a $C_1$-$C_{10}$ alkyl or aryl group.

A "detectable product" of a reaction is a compound or composition that accumulates, in the context of the present technology, in the presence of an analyte as a product of the described catalytic reaction. The accumulation of the detectable product is identified or quantified by any suitable instrumentation or device. For example, the product may be detectable by a change in color, such as a change in absorbance at any wavelength(s), or by fluorescence. Examples of other detectable differences include: a change in conductance; a change in refraction index; a change in transmittance; rotational change in polarized light (polarimetry); other spectroscopic methods; a change in rheology; a change in fluorescence (FÖrster) resonance energy transfer; a change in surface plasmon resonance; electrophoresis; or any other analytical method useful for detection or quantification of a chemical compound.

A large variety of instrumentation is commercially-available, such as plate readers or other spectrophotometric or fluorescence spectroscopy instruments that can be used to identify accumulation of a detectable product in multi-well plates; microplates; cuvettes; tubes, including microcentrifuge tubes; microfluidics; and any other physical device containing one or more discrete reactions. Likewise any assay can be automated, either partially or fully. Examples of automated platforms for use in conducting various assays as described herein include the Freedom EVO® or Fluent® platforms or GenePaint™ system (Tecan Trading AG, Switzerland).

As used herein, the term "array" refers to reagents, for example for implementing the assays described herein, located at two or more discrete, identifiable and/or addressable physical locations. In one aspect, any assays according to any aspect described herein are implemented on an array. Arrays are particularly useful in implementing high-throughput assays, such as analyte or genetic detection assays. In one aspect, an array is an apparatus having two or more discrete, identifiable reaction chambers, such as, without limitation, a 96-well dish, in which reactions comprising identified constituents are performed. In an exemplary aspect, selectivity components, such as analyte-specific antibodies, antibody fragments, nucleic acids, or nucleic acid analogs, for binding one or more target analytes, are immobilized onto a substrate in a spatially addressable manner so that selectivity components (e.g., antibodies, antibody fragments, aptamers, or any other binding reagent that binds specifically to a target compound or composition) are located at two or more a different and (addressable) identifiable location on the substrate. Substrates include, without limitation, multi-well plates, microfluidic systems, silicon chips, and beads. For substrates with two or more addressable locations on a single substrate, such as a chip or multi-well plate, the same and/or different selectivity components can be placed at discrete locations on the substrate. An assay may be multiplexed, wherein binding of different target analytes to different selectivity components are independently identifiable, such as by producing a different detection signal, such as by producing different colors, or, for fluorochromes, having different excitation and or emission wavelengths and/or intensities. Binding events for each different selectivity component in multiplexed reactions can be detected at the same time or at a different time, for example by producing different emission wavelengths using the same excitation spectrum, or by measuring spectra at different time points. In one aspect, an array is a multi-well plate containing two or more wells with the described selectivity components for binding specific target analytes. As such, reagents, such as probes and primers may be bound or otherwise deposited onto or into specific locations on an array. In another aspect, each addressable location of an array, such as, each well of a multi-well plate, comprises the same or different set of reagents used for detection of an analyte, such as the reagents described herein as being useful for quantification of Pd. As indicated different amounts of reagents may be used at different locations of the array to serve as controls, to conduct different reactions, or to conduct reactions using different amounts of the reagent to, for example, expand the dynamic range of the assay. Reagents may be in any suitable form, including, without limitation: in solution, dried, lyophilized, or glassified. When linked covalently to a substrate, such as an agarose bead or silicon chip, a variety of linking technologies are known for covalently attaching chemical moieties to such substrates, such as selectivity components such as ligands, antibodies or fragments thereof, aptamers, or genetic recognition reagents. Linkers and spacers for use in linking peptides, nucleic acids, peptide nucleic acids, other nucleic acid analogs, and other selectivity components are broadly known in the chemical and array arts and for that reason are not described herein. Informatics and/or statistical software or other computer-implemented processes for analyzing array data are known in the art or are readily developed by a skilled practitioner.

Therefore, in one aspect an array is provided for detection of or quantification of Pd content in a sample. The array comprises at more than one discrete, addressable locations, a composition comprising resorufin allyl ether (RAE), and optionally ethanol, $NH_4OAc$, Pd, and/or $NaBH_4$, and optionally wherein the NaBH is in different amounts at different locations of the array. In another aspect, an array is provided for detection of an analyte using horseradish peroxidase or another peroxidase. The array comprises at more than one discrete, addressable locations, a peroxidase, such as horseradish peroxidase (HRP), $H_2O_2$, a colorimetric substrate for the peroxidase, such as Amplex Red, and a boronic acid, such as $PhB(OH)_2$, and optionally wherein the $H_2O_2$ is present in different amounts at different locations of the array. Also provided are kits comprising one or more vessels, or an array, comprising reagents for conducting an assay as described herein.

EXAMPLES

As discussed above catalysis-based assays require 'fine tuning' of conditions to avoid signal saturation, substrate depletion, and nonlinear assay performance. Therefore, provided herein is a rapid, colorimetric method for palladium detection, employing the cleavage of an allylic ether from the chemodosimeter, allyl resorufin ether (ARE), to release resorufin, shifting the color of the solution from yellow to purple. Uniquely, the method exhibits an autonomous, reversible stalling under certain conditions, allowing for the reaction to stop after a controlled amount of time. Fine-tuning reaction components allows the reaction to continue for longer periods of time. This new method, through serial additions of $NaBH_4$ to a single solution, can quantify palladium concentrations ranging over 5 orders of magnitude, rivaling ICP-MS and ICP-OES. The deallylation of ARE to form resorufin was tested successfully in residual palladium detection in pharmaceuticals, ores, and organic polymers. The method is colorimetric, allowing for the users to visually estimate the quantities palladium in samples without instruments.

Example 1: Optimization of RAE as a Substrate

Figure 2:
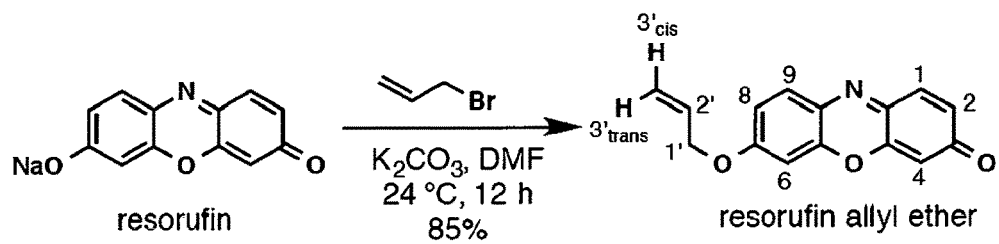
FIG. 2: Preparation of resorufin allyl ether (RAE).

Synthesis of RAE:
FIG. 2 shows a basic schematic of the preparation of resorufin allyl ether (RAE). A solution of resorufin sodium salt (200 mg, 0.850 mmol) in DMF (5 mL) was treated with $K_2CO_3$ (356 mg, 2.55 mmol, 3.0 equiv) followed by allyl bromide (1.4 mL, 0.94 mmol, 1.1 equiv) in DMF (1 mL) at 24° C. and stirred at the same temperature for 12 h. The reaction mixture was then quenched with water (100 mL), and the resulting mixture was filtered through a coarse fritted funnel. The resulting solid was washed with water (3×100 mL) and cold hexanes (100 mL). The solid was recrystallized from ethyl acetate and hexanes, affording resorufin allyl ether (181 mg, 0.71 mmol, 85% yield) as a dark red-orange solid.

Figure 3:
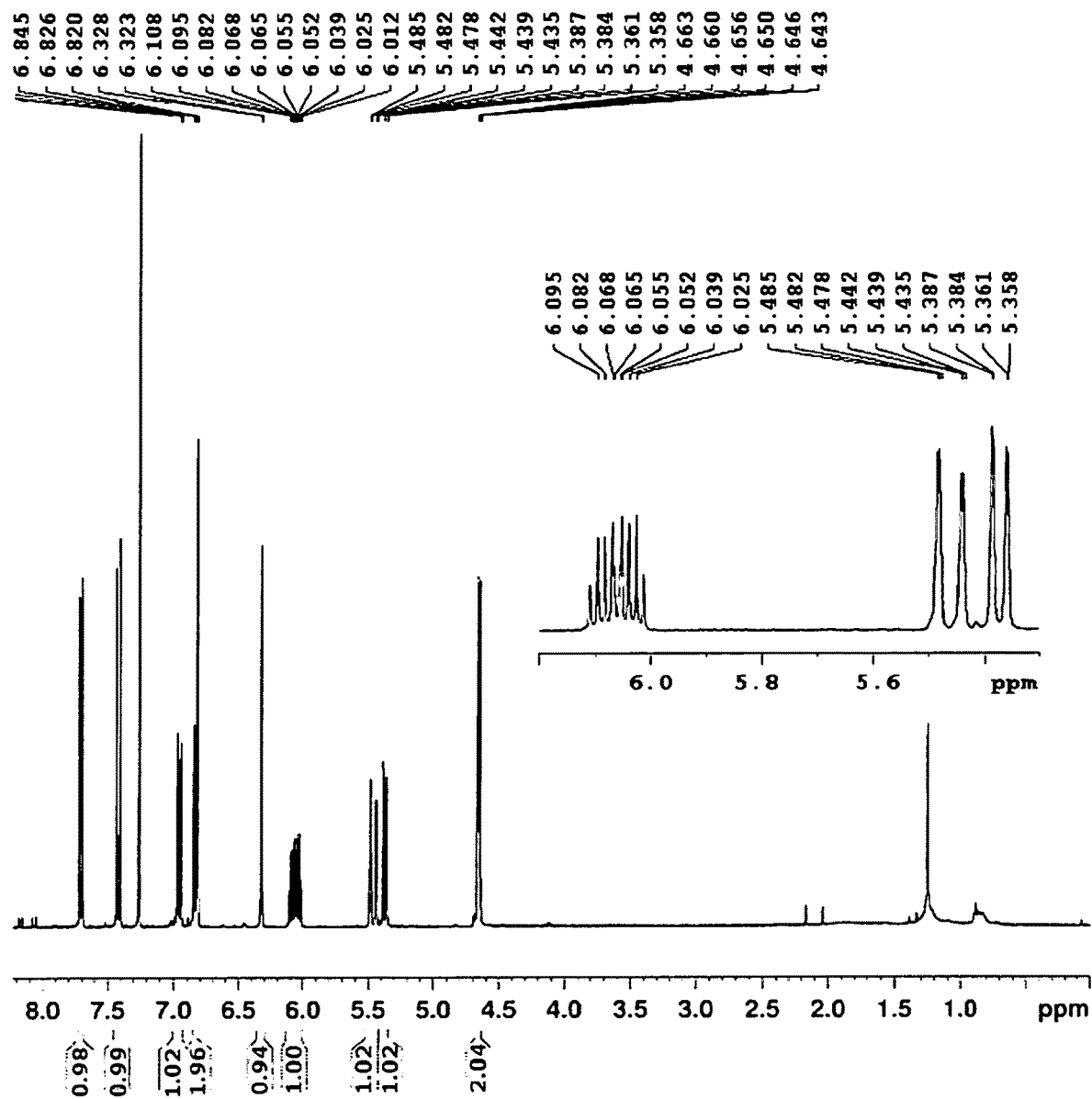
FIG. 3: $^1H$ NMR spectrum of RAE: $CDCl_3$, 293K, 400 MHz.
Figure 4:
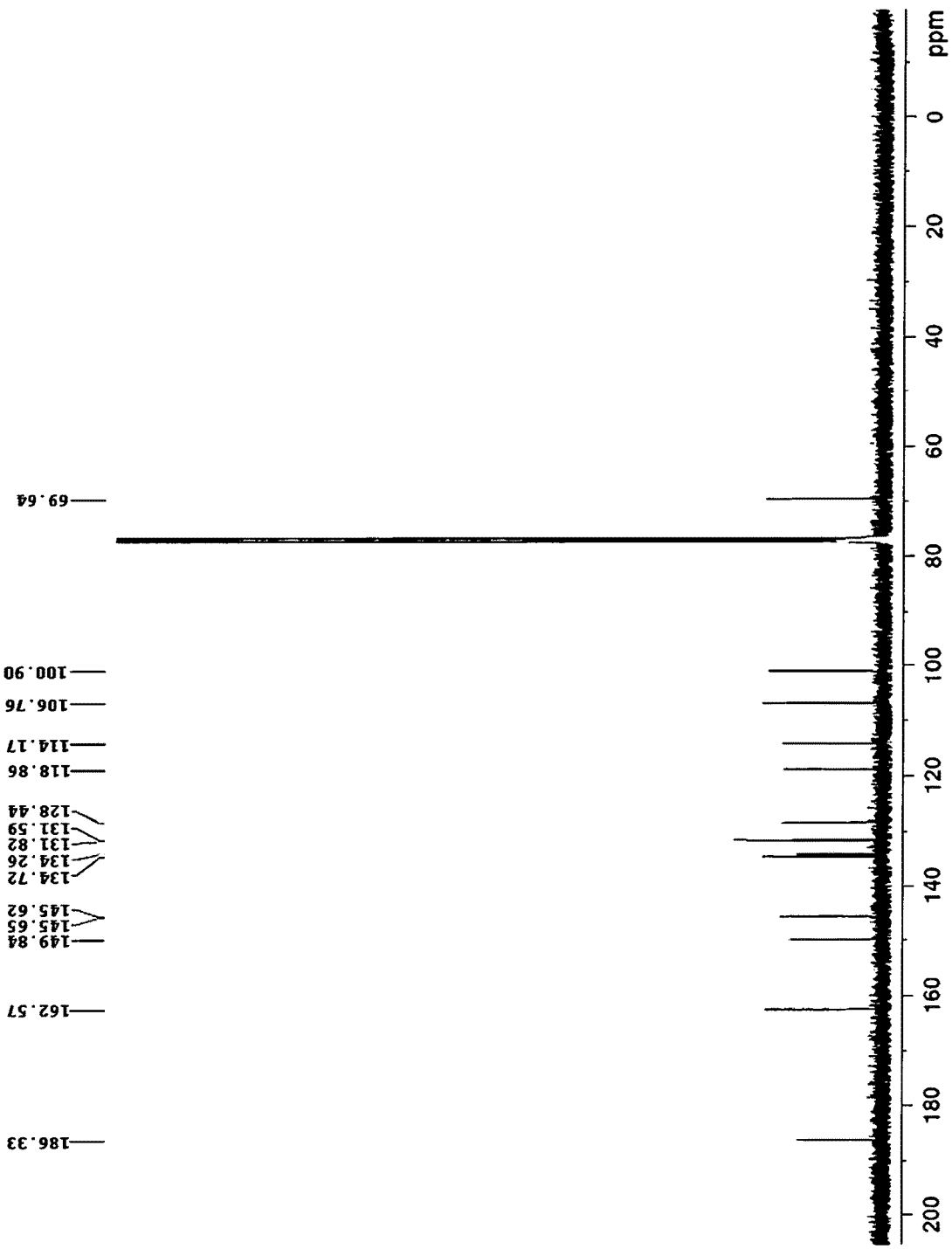
FIG. 4: $^{13}C$ NMR spectrum of RAE: $CDCl_3$, 293K, 75 MHz.

Data for resorufin allyl ether: Rf=0.34 (50% ethyl acetate in hexanes); m.p.: 210.3-211.6° C. (decomp); IR: 2960, 2873, 1733 (C=O), 1466, 1369, 1151, 1031, 955.45, 862, 785, 735 $cm^{-1}$; $^1H$ NMR (400 MHz, CDCls, 293 K, FIG. 3): δ 7.71 (d, J=8.8 Hz, 1H, Ar), 7.42 (d, J=10.2 Hz, 1H, Ar), 6.96 (dd, J=8.8, 2.4 Hz, 1H, Ar), 6.84 (dd, J=10.2, 2.0 Hz, 1H, Ar), 6.82 (d, J=2.4 Hz, 1H, Ar), 6.32 (d, J=2.0 Hz, 1H, Ar), 6.06 (ddt, J=17.2, 10.2, 5.1 Hz, 1H, 2'-H), 5.46 (ddt, J=17.2, 3.0, 1.5 Hz, 1H, 3'-Hcis), 5.37 (ddt, J=10.2, 3.0, 1.5 Hz 1H, 3'-Htrans), 4.65 (ddt, J=5.1, 1.5, 1.5 Hz, 2H, 1'-H). $^{13}C$ NMR (75 MHz, $CDCl_3$, 293 K, FIG. 4): δ 186.3, 182.6, 149.8, 145.65, 145.62 134.7, 134.3, 131.8, 131.6, 128.4, 118.9, 114.2, 106.8, 100.9, 69.6; HRMS: (ESI+) calcd for $C_{15}H_{11}NO_3$ [M+H]=254.0814, found 254.0798.

Figure 5:
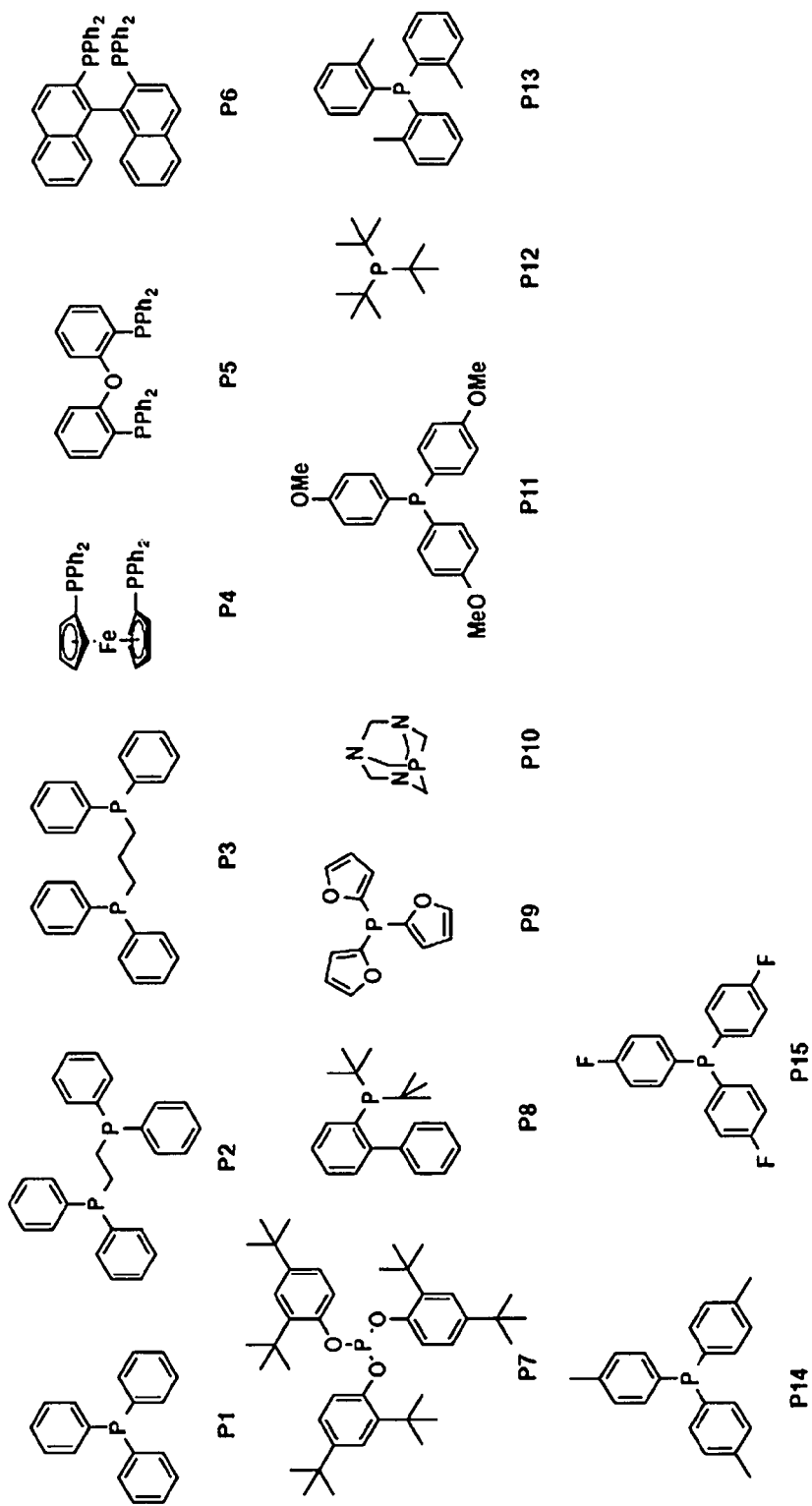
FIG. 5: Phosphines screened for deallylation of RAE to resorufin.

Determination of Optimal Phosphine Ligand for Deallylation of RAE:

To separate scintillation vials was added triphenylphosphine (P1, FIG. 5) (26.2 mg, 0.100 mmol), 1,2-bis(diphenylphosphino)ethane (P2) (39.5 mg, 0.100 mmol), 1,3-bis(diphenylphosphino)propane (P3) (41.6 mg, 0.100 mmol), 1,1'-bis(diphenylphosphino)ferrocene (P4) (55.4 mg, 0.100 mmol), bis(2-diphenylphosphinophenyl)ether (P5) (53.8 mg, 0.100 mmol), racemic-2,2'-bis(diphenylphosphino-1,1'-binaphthalene (P6) (62.2 mg, 0.100 mmol), tris(2,4-di-tert-butylphenyl)phosphite (P7) (64.8 mg, 0.100 mmol), (2-biphenyl)-di-tert-butylphosphine (P8) (29.6 mg, 0.100 mmol, 8), tri(2-furyl)phosphine (TFP) (P9) (23.7 mg, 0.100 mmol), 1,3,5-triazaphosphaadamantane (P10) (15.6 mg, 0.100 mmol), tris(4-methoxyphenyl)phosphine (P11) (35.2 mg, 0.100 mmol), tri-tert-butylphosphonium tetrafluoroborate (P12) (29.8 mg, 0.100 mmol), tri(o-tolyl)phosphine (P13) (30.3 mg, 0.100 mmol), tri(p-tolyl)phosphine (P14) (30.6 mg, 0.100 mmol), and tris(4-fluorophenyl)phosphine (P15) (31.2 mg, 0.100 mmol), and DMSO (5.0 mL, [phosphine ligand]=20 mM). To a separate vial, an aliquot of previously prepared solutions (48 μL) were diluted in DMSO (252 μL, [phosphine]-3.2 mM). Two-fold serial dilutions were performed to afford 1600, 800, 400, 200, and 100 μM phosphine ligand solutions in DMSO.

Figures 6, 7:
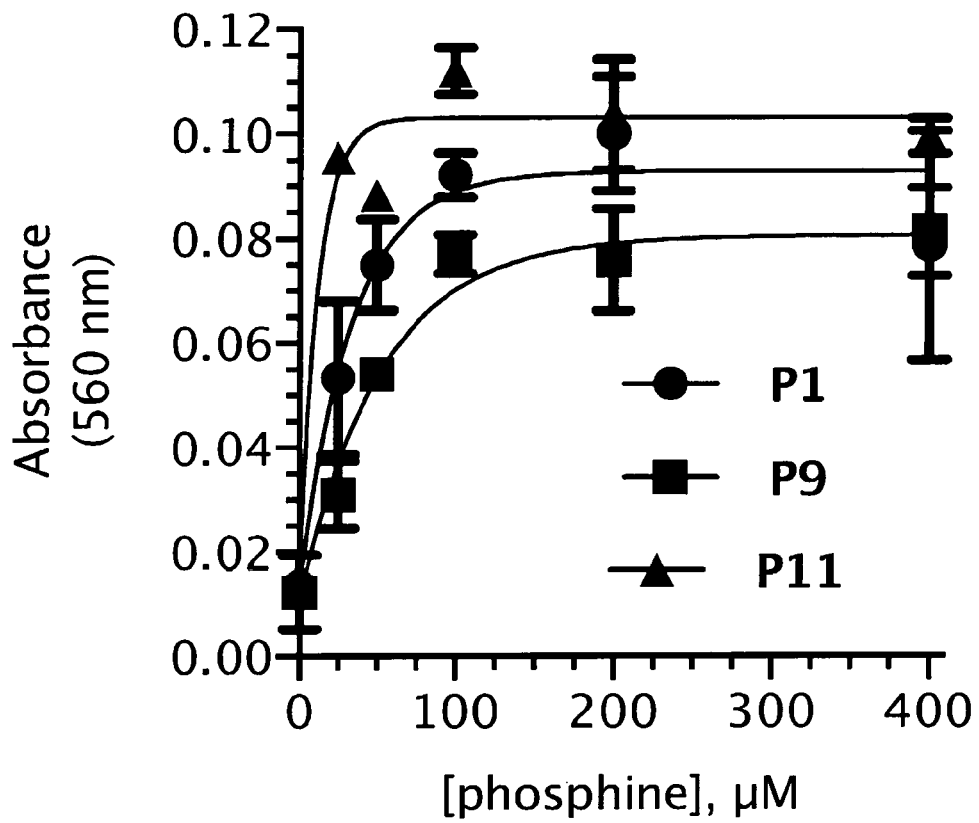
FIG. 6: Determination of optimal phosphine ligand for deallylation of RAE.
FIG. 7: Rescreening P1 (black circles), P9 (red squares), P11 (blue triangles) from phosphine screen. 200 μM RAE, 40 ppb $Pd^{2+}$, 300 μM $PhCH_2NH_2$, 0-400 μM phosphine, 10 mM $NaBH_4$, EtOH, 25° C., 60 min, n=1. P9 was selected as the phosphine of choice as it could store solutions for, 6 months without degradation in the presence of 250 ppm BHT.

The reaction cocktail was prepared by mixing EtOH (23.6 mL), 800 μM RAE in EtOH (683 μL), $PhCH_2NH_2$ (621 μL), and 2.5 M $NaBH_4$ in 10 N NaOH (99 μL) at 0° C. The resulting solution (175 μL) was distributed to each well of a black round-bottom 96-well plate. The phosphine solutions (25 μL) described above were added to each well affording final concentrations of 400, 200, 100, 50, 25, and 12.5 μM phosphine. To each well was added 1 ppm palladium standard solution in 5% TraceMetal nitric acid (10 μL, affording a final concentration of 40 ppb Pd). Fluorescence (excitation 490 nm, emission 510-570 nm) was recorded after 1, 30, and 60 min. The ratio of fluorescence was compared to 400 μM triphenylphosphine as a control and is reported. The result is shown in FIG. 6.

Rescreening of Active Phosphine Ligands:

The reaction cocktail was prepared by mixing EtOH (23.6 mL), 800 μM RAE in EtOH (683 μL), $PhCH_2NH_2$ (621 μL), and 2.5 M $NaBH_4$ in 10 N NaOH (99 μL) at 0° C. The resulting solution (175 μL) was distributed to each well of a black round-bottom 96-well plate. The phosphine solutions of P1, P9, and P11 (25 μL) described above were added to each well affording final concentrations of 400, 200, 100, 50, 25, and 12.5 μM phosphine. To each well was added 1 ppm palladium standard solution in 5% TraceMetal nitric acid (10 μL, affording a final concentration of 40 ppb Pd). Absorbance (560 nm) was measured after 60 min. The result is shown in FIG. 7.

Figure 8:
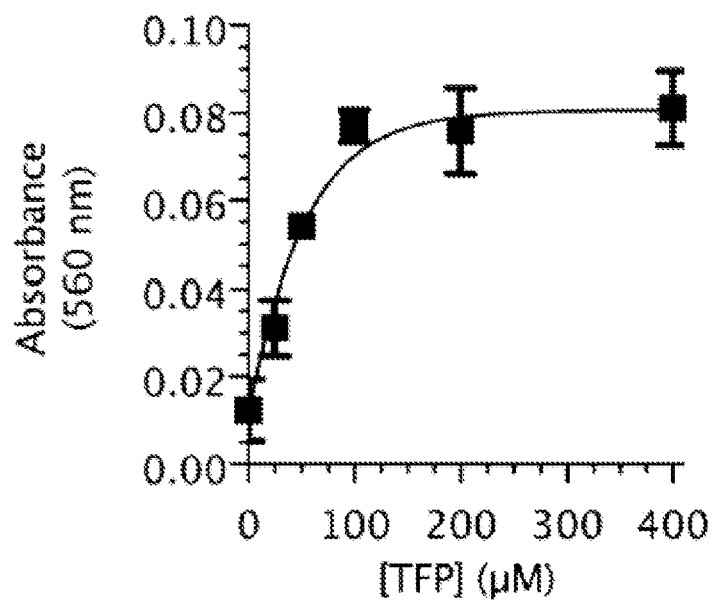
FIG. 8: Screening for optimized TFP (P9) concentration dependence. Reaction conditions were 200 μM RAE, 40 ppb $Pd^{2+}$, 300 μM $PhCH_2NH_2$, 10 mM $NaBH_4$, 0-400 μM TFP, EtOH, 24° C., 60 min. n=3.

Determination of Optimal Tri-(2-Furyl)Phosphine (P9) Concentration:

In a scintillation vial was added TFP (P9) (23.2 mg, 0.100 mmol) and DMSO containing 250 ppm BHT (5.0 mL; [TFP]=20 mM). To a white chemically resistant plate was added this solution (192 μL) and DMSO (108 μL, [TFP]= 12.8 mM). From this solution, 2× serial dilutions in DMSO were performed to concentrations of 0.400, 0.200, 0.100, 0.0500, 0.0250, and 0 mM. The reaction cocktail was prepared by mixing EtOH (7.6 mL), 800 μM RAE in EtOH (220 μL), benzylamine (200 μL) and 2.5 M $NaBH_4$ in 10 N NaOH (32 μL) at 0° C. The solution (175 μL) was transferred to each reaction well in a 96-well clear, flat-bottom absorbance plate. The TFP solutions (25 μL) described above were added to each well for final concentrations of 400, 200, 100, 50, 25, and 12.5 μM. A 20 ppb Pd2+ standard solution in 5% TraceMetal $HNO_3$ (10 μL) was added to each well. The assay was performed at 23° C., and absorbance (560 nm) was measured after 1 and 60 min using a Modulus II Microplate Multimode Reader. The result is shown in FIG. 8.

Preparation of Stock Metal Solutions:

To separate scintillation vials were added $AgNO_3$ (425 mg, 2.50 mmol), $AuCl_3$ (759 mg g, 2.50 mmol), $CdCl_2$ (459 mg, 2.50 mmol), $CoCl_2$ (325 mg, 2.50 mmol), $CrCl_3$ (396 mg, 2.50 mmol), $FeCl_3$ (406 mg, 2.50 mmol), $HgCl_2$ (679 g, 2.501 mmol), $MnCl_2$ (315 mg, 2.50 mmol), $NiCl_2$ (324 mg, 2.50 mmol), $PtCl_2$ (665 mg, 2.50 mmol), $ZnCl_2$ (341 mg, 2.50 mmol), $Sr(NO_3)_2$ (529 mg, 2.50 mmol), $IrCl_3$ (745 mg, 2.50 mmol) and $Cu(NO_3)_2$ (336 mg, 2.50 mmol) and ultrapure $H_2O$ (2.5 mL; [metal]=1.0 M). To separate scintillation vials were added a metal solution (50 μL) that was prepared above, and ultrapure $H_2O$ (4.95 mL; [metal]=10 mM. Two serial dilutions of the metal solution (20 μl) with ultrapure water (180 μL) were carried out to afford a final concentration of 100 μM.

In separate scintillation vials was added either $RuCl_3$ (10.4 mg, 50.1 μmol) or $RhCl(PPhs)_3$ (45 mg, 50 μmol) and ultrapure $H_2O$ (5.00 mL) To separate scintillation vials was added these solutions (100 μL) and Ultrapure (9.9 mL, [metal]=100 μM).

A 10 μM solution of $Pd(NO_3)_2$ was prepared through the serial dilution of a 100 ppm $Pd^{2+}$ standard solution in 10% nitric acid (10 μL) with ultrapure water (990 μL).

Determination of Metal Selectivity for RAE:

The reaction cocktail was prepared by mixing 800 mM $NH_4OAc$ in EtOH (15 mL), 800 μM RAE in EtOH (600 μL), 3.0 M TFP (P9) in DMSO, stabilized by 250 ppm BHT in DMSO (1.2 mL) and 0.1 M $NaBH_4$ in 10 N NaOH (450 μL) at 0° C. The solution (180 μL) was distributed to each well in a clear flat-bottom 96-well plate. The deallylation reaction was performed in triplicate by transferring the 100-μM metal solutions or 10 μM in the case of $Pd^{2+}$ (20 μL) to the reaction cocktail. The well plates were incubated at 25° C. Absorbance (560 nm) was measured 1 min and 1 h after the transfer using a Modulus II Microplate Multimode Reader. After 1 h, wells corresponding to Au, Ag, Hg, Pd, and Pt were transferred to a 96-well black fluorescence well plate and fluorescence (excitation 525 nm, emission 580-640 nm) was measured using a Modulus II Microplate Multimode Reader.

Determination of Interference by Other Metals:

Metal solutions were prepared as in "Metal selectivity screen". On a black 96-well plate was added each 100 μM solution of metals in ultrapure $H_2O$ (990 μl) that was prepared as described above and a 100 μM solution of $Pd^{2+}$ in ultrapure $H_2O$ (10 μL).

Figure 9A:
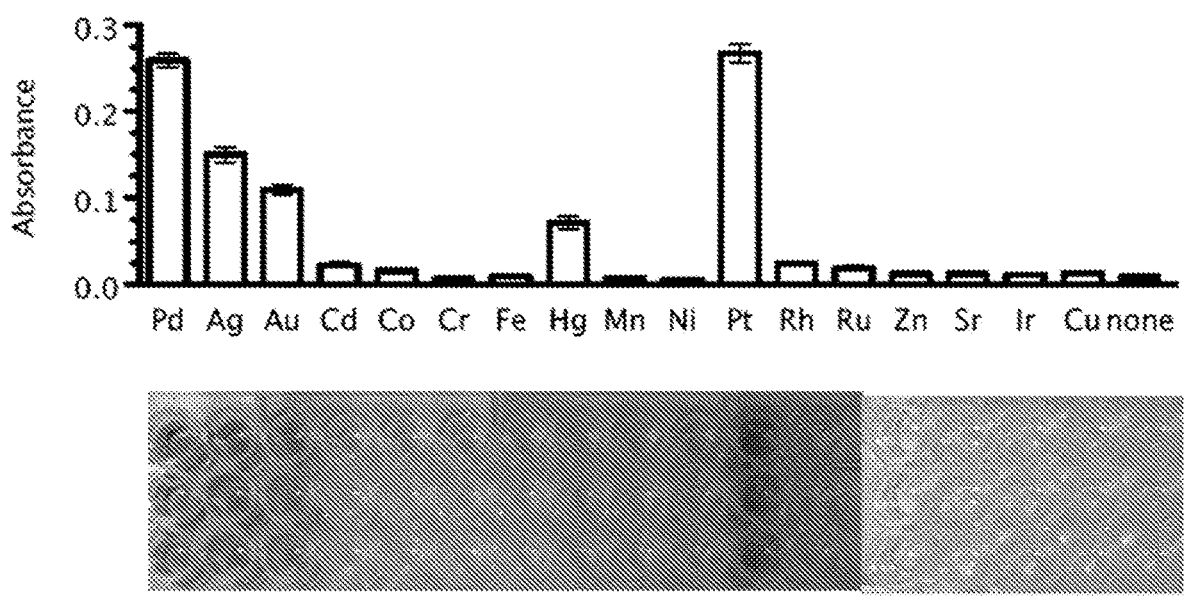
FIGS. 9A-9C.
Figure 9B:
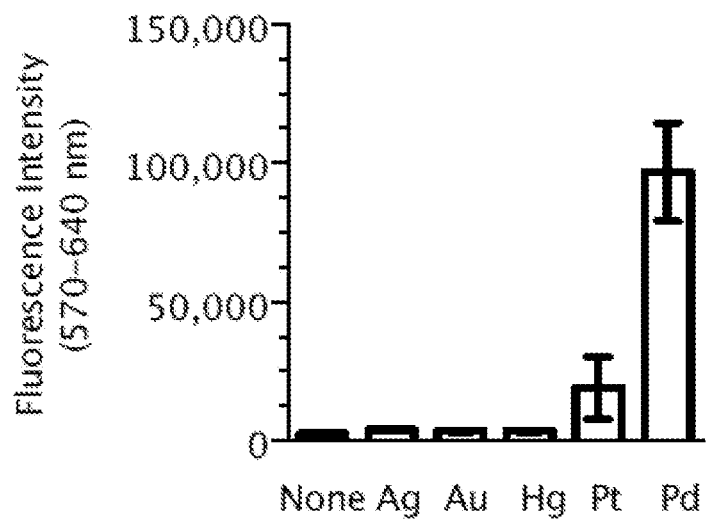
Figure 9C:
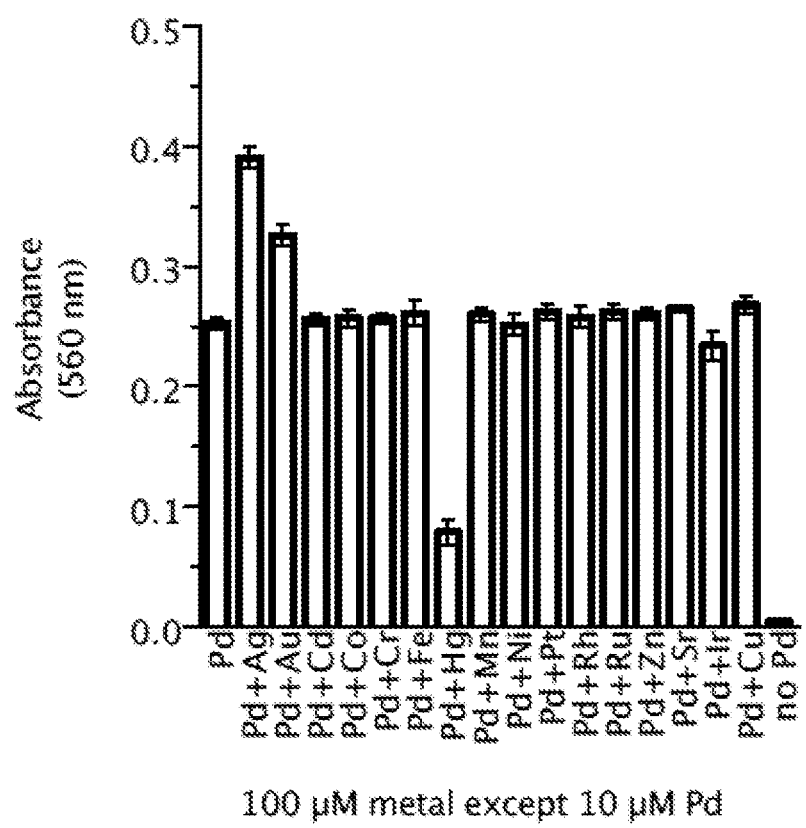

The reaction cocktail was prepared by mixing 800 mM $NH_4OAc$ in EtOH (15 mL), 800 μM RAE in EtOH (600 μL), 3.0 M TFP (P9) in DMSO stabilized by 250 ppm BHT (1.2 mL) and 0.1 M $NaBH_4$ in 10 N NaOH (450 μL) at 0° C. The solution (180 μL) was distributed to a clear flat-bottom 96-well plate. The deallylation reaction was performed in triplicate by transferring the metal solutions described above (20 μL) to the reaction cocktail on the plate. The well plates were incubated at 25° C. Absorbance (560 nm) was measured 1 min and 1 h after the transfer using a Modulus II Microplate Multimode Reader. The result is shown in FIGS. 9A-9C.

Figure 10:
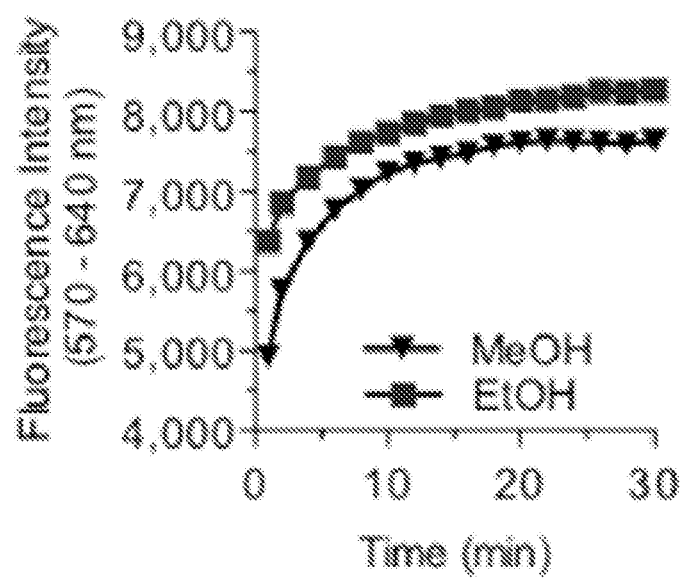
FIG. 10: Deallylation of RAE employing EtOH or MeOH as solvent under the following conditions: 29 μM RAE, 200 μM TFP, 5 mM $NaBH_4$, 800 mM $NH_4OAc$, EtOH or MeOH, 24° C., 30 min. n=1.

Testing Effect of Alcohol Solvent on Deallylation:

To a 2-mL Eppendorf tube was added 800 mM $NH_4OAc$ in ROH (1 mL, R=Me, Et). To this solution was added 3 mM TFP stabilized by 250 ppm BHT in DMSO (80 µL) and 800 µM RAE in EtOH (40 µL). To the resulting solutions was added either 0 or 500 ppb $Pd^{2+}$ in 5% $HNO_3$ (20 µL) and 0.1 M $NaBH_4$ in 10 N NaOH (50 µL). The solutions (200 µL) were transferred to a black 96-well fluorescence plate and fluorescence (excitation 525 nm, emission 570-640 nm) was recorded every 1 min for 30 min. The result is shown in FIG. 10.

Figure 11:
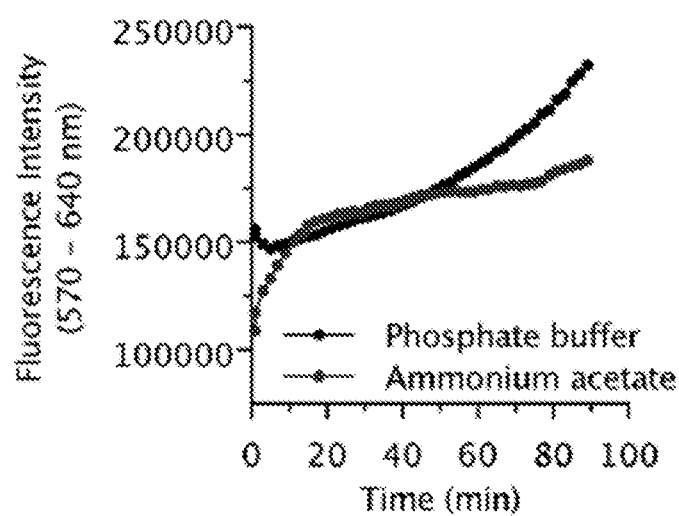
FIG. 11: 20 μM APE, 10 ppb $Pd^{2+}$, 80 μM TFP (P9), 600 mM $HPO_4^{2-}$ or $NH_4OAc$, 25° C., 90 min, 20% v/v EtOH/$H_2O$.

Testing Allyl Pittsburgh Green Ether (APE) for Autonomous Stalling with NH4OAc:

The acetate-containing reaction cocktail was prepared by mixing $NH_4OAc$ (440 mg, 5.71 mmol) with EtOH (2 mL) and ultrapure $H_2O$ (7.5 mL), 800 µM APE in DMSO (250 µL), and 3.2 mM TFP in DMSO stabilized with 250 ppm BHT (250 µL). In a separate vial, the phosphate-containing reaction cocktail was prepared by mixing 1.2 M potassium phosphate pH 7 buffer (5 mL), EtOH (2 mL), ultrapure $H_2O$ (2.5 mL), 800 µM 1a in DMSO (250 µL), and 3.2 mM TFP (P9) in DMSO stabilized with 250 ppm BHT (250 µL). The reaction cocktail (1 mL) was added to 2-mL Eppendorf tubes. To half of the samples for each buffer was added 5% TraceMetal $HNO_3$ (20 µL) as a control. To the other half of the samples was added 50 ppb $Pd^{2+}$ in 5% TraceMetal $HNO_3$ (20 µL). To all samples was added 0.5 M $NaBH_4$ in 10 N NaOH (20 µL). The samples were mixed and added (200 µL) to a 96-well black fluorescence well plate. Fluorescence (excitation 525 nm, emission 570-640 nm) was measured every 2 min for 60 min using a Modulus II Microplate Multimode Reader. The result is shown in FIG. 11.

Figure 12:
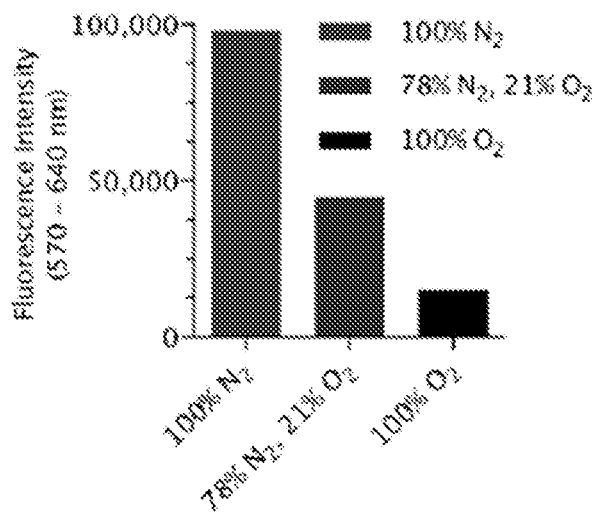
FIG. 12: Analysis of stalling under inert atmosphere. Conditions: 29 μM RAE, 200 μM TFP, 1 mM $NaBH_4$, 100 ppb $Pd^{2+}$, 800 mM $NH_4OAc$, 25° C., 100% $N_2$, 100% $O_2$, air (1 atm), EtOH, 15 min, n=1.

Deallylation Under Inert Atmosphere:

Three separate round-bottom flasks were vacuumed and sealed with a rubber stopper. Either a balloon of $N_2$, $O_2$, or air (78% $N_2$, 21% $O_2$) was then attached with a needle. A scintillation vial was treated with 800 mM $NH_4OAc$ in EtOH (9 mL), 3 mM TFP in DMSO stabilized by 250 ppm BHT (720 µL), and 800 µM RAE in EtOH (360 µL). Aliquots (2 mL) of this solution were added to each flask followed by 1 ppm $Pd^{2+}$ in 5% $HNO_3$ (100 µL) and 40 mM $NaBH_4$ in 10 N NaOH (50 µL) via syringe. After 15 min, aliquots (200 µL) of each solution were transferred to a black 96-well plate, and fluorescence (excitation 525 nm, emission 580-640 nm) was measured using a Modulus II Microplate Multimode Reader. The result is shown in FIG. 12.

Figure 13:
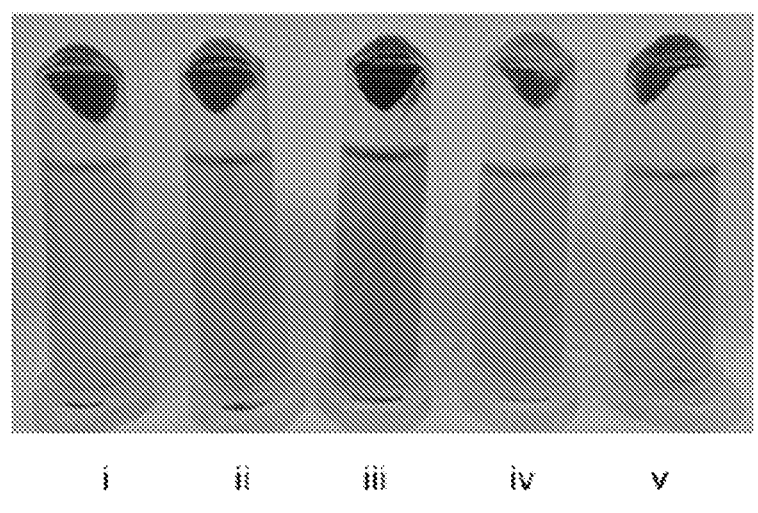
FIG. 13: Analysis of palladium ore samples using colorimetric assay with ARE. Conditions: 29 μM RAE, 200 μM TFP, 800 mM $NH_4OAc$, 75 mM $NaBH_4$, 200 mg milled ore sample, EtOH, 25° C., 20 min. Sample i contains 0.030% palladium by weight, Sample ii contains 0.068% palladium by weight, Sample iii contains 0.094% palladium by weight. Samples iv and v contain no palladium. Palladium concentrations were determined by aqua regia digestion and analysis (K. P. Carter, A. M. Young, A. E. Palmer, Fluorescent sensors for measuring metal ions in living systems. *Chemical Reviews* 114, 4564-4601 (2014)).

Analysis of Ores:

Ore samples used were provided by Stillwater Mining Co. and were previously analyzed for palladium content using APE following aqua regia digestion and by solid-state palladium extraction Initial attempts to directly analyze the samples with RAE failed, likely due to difficulty in palladium extraction from the rock samples in the short reaction time. Whereas the previous method with APE could extract palladium and the reaction would run indefinitely, the new method stalls before a signal could be recovered and before significant palladium was extracted. To alleviate this with the single cocktail, palladium was extracted using TFP in DMSO followed by the addition of RAE and $NH_4OAc$-containing EtOH. $NaBH_4$ was subsequently added to the samples. To 2 mL Eppendorf tubes were added ore samples (75 mg, Note: These samples contained ranges of 0 to 0.068% Pd by weight as determined by previous analysis using APE (20) and 3 mM TFP in DMSO stabilized by 250 ppm BHT (145 µL). Samples were sonicated for 60 s. To a scintillation vial was added 800 mM $NH_4OAc$ in EtOH (6.48 mL) and 800 µM RAE in EtOH (259 µL). This solution (1.86 mL) was added to each Eppendorf tube containing ore samples. To each sample was added 2.5 M $NaBH_4$ in 1 N NaOH (20 µL). The samples were incubated at 25° C. for 5 min. An additional 2.5 M $NaBH_4$ in 1 N NaOH (20 µL) was added and again the samples were incubated for 5 min. To each sample was again added 2.5 M $NaBH_4$ in 1 N NaOH (20 µL, 75 mM $NaBH_4$ final) and the samples were incubated for 5 min, centrifuged using a Galaxy II Mini benchtop centrifuge for 20 s, and the resulting slurry was recorded with a photograph obtained under ambient light. The result is shown in FIG. 13.

Analysis of Polymers by Colorimetric Detection:

The colorimetric assay was then applied to the detection of residual Pd Impurities in organic polymers, a problem of increasing concern in the specialty chemical arena, where such impurities can compromise the performance characteristics of organic polymers prepared by either batch preparation or flow synthesis polymerization. Various polymer samples, prepared by either batch or flow synthesis with varying amounts of palladium catalyst by the Krebs group (Table 1, see below), were dissolved in either CHCl3 or PhMe and analyzed using RAE.

TABLE 1

Anaylsis of polymers prepared by palladium catalysis

| Polymer Sample | Polymerization Method (scale) | Mol % $(Pd)_2(dba)_3$ | Reaction time |
|---|---|---|---|
| Sample 1 | Batch (0.3 g) | 3 | 24 h |
| Sample 2 | FSP* (0.3 g) | 1 | 30 min |
| Sample 3 | FSP (0.3 g) | 3 | 30 min |
| Sample 4 | FSP (0.3 g) | 5 | 30 min |
| Sample 5 | FSP (0.3 g) | 3 | 15 min |
| Sample 6 | FSP (0.3 g) | 3 | 45 min |
| Sample 7 | FSP (0.3 g) | 3 | 30 min |

*FSP = Flow synthesis polymerization

Addition of polymer solutions to a reaction cocktail containing RAE was unsuccessful (data not shown), either due to the lack of solubility of the polymer itself or due to interference from the polymer.

Preparation of Polymer Solutions:

Solutions of polymers provided by the Krebs laboratory (Technical University of Denmark) were dissolved in either toluene ("Sample 2") or CHCl3 ("Sample 1, 3, 4, 5, 6, 7") to afford concentrations of 1,000 µg/mL (1,000-ppm) of polymer.

Figure 14:
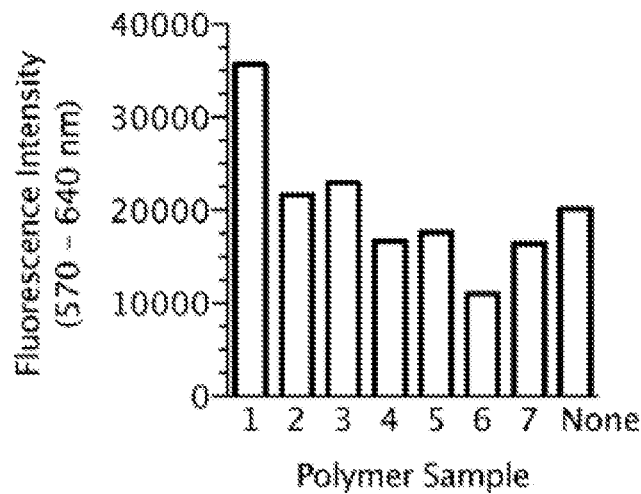
FIG. 14: Analysis of polymers after digestion with aqua regia. 29 μM RAE, 5 ppm polymer, 200 μM TFP, 800 mM $NH_4OAc$, 25 mM $NaBH_4$, 25° C., EtOH, 30 min, n=1.

Analysis of Polymers by Aqua Regia Digestion:

To separate 2-dram vials were added polymer solution (400 µL), placed under a stream of air at 25° C. and evaporated to dryness. To these vials was added freshly prepared aqua regia (100 µL) and the samples were allowed to digest for 16 h at 25° C. To each vial was added ultrapure $H_2O$ (900 µL). Reaction cocktail described in "General protocol for deallylation of RAE" (1 mL) was added to 2-mL Eppendorf tubes and to this solution was added either 10% aqua regia or polymer suspension in 10% aqua regia (20 µL, [polymer]=5 ppm) and 2.5 M $NaBH_4$ in 10 N NaOH (20 µL). Each solution (200 µL) was transferred to a black 96-well fluorescence plate and the fluorescence (excitation 525 nm, emission 570-640 nm) was measured after 30 min. The result is shown in FIG. 14.

Determination of Interference by Polymers:

To separate 2-dram vials was added 1000 ppm "Sample 4" in CHCl3 (400 µL). Vials were placed under a stream of air at 25° C. and evaporated to dryness. To these vials was added freshly prepared aqua regia (100 μL) and the samples were allowed to digest for 16 h at 25° C. To each vial was added ultrapure $H_2O$ (900 μL).

Figure 15:
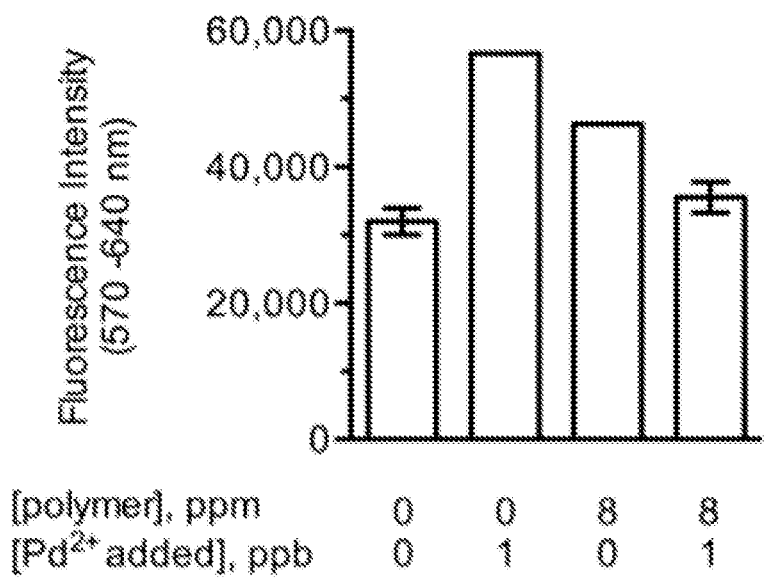
FIG. 15: Interference by polymers on analysis with RAE. 29 μM RAE, 0-8 ppm polymer, 0-1 ppm $Pd^{2+}$, 200 μM TFP, 25 mM $NaBH_4$, EtOH, 24° C., 30 min.

Reaction cocktail described in "General protocol for deallylation of RAE" (1 mL) was added to 2-mL Eppendorf tubes and to this solution was added either 10% aqua regia or polymer suspension in 10% aqua regia (20 μL, [polymer] =8 ppm), to half of the samples was added $H_2O$, to the other half was added 50 ppb $Pd^{2+}$ in $H_2O$ (20 μL), and 2.5 M $NaBH_4$ in 10 N NaOH (20 μL). Each solution (200 μL) was transferred to a black 96-well fluorescence plate and the fluorescence (excitation 525 nm, emission 570-640 nm) was measured every 2 min for 30 min. The result is shown in FIG. 15.

To alleviate the problem, we turned to acid digestion, removing aliquots of the polymer solutions, evaporating them to dryness, and resuspending them in 5% $HNO_3$. Heating the samples affected a rapid extraction of palladium, and subsequent analysis using RAE revealed relative palladium concentrations in each polymer. The highest palladium-containing polymer was subjected to further analysis, highlighting the use of RAE as a colorimetric chemodosimeter for analysis of digested polymers.

Heat-Assisted Polymer Analysis:

To separate 2-dram vials were added 1000 ppm polymer solutions in toluene ("Sample 2") or $CHCl_3$ ("Samples 1, 3, 4, 5, 6, 7") (400 μL). The vials were placed under a stream of air at 25° C. and evaporated to dryness. To each vial was added 5% TraceMetal $HNO_3$ (500 μL) and the resulting suspensions (800 ppm polymer) were loosely sealed with threaded tape and screw caps and incubated in a 70° C. water bath for 3 h.

Figure 16:
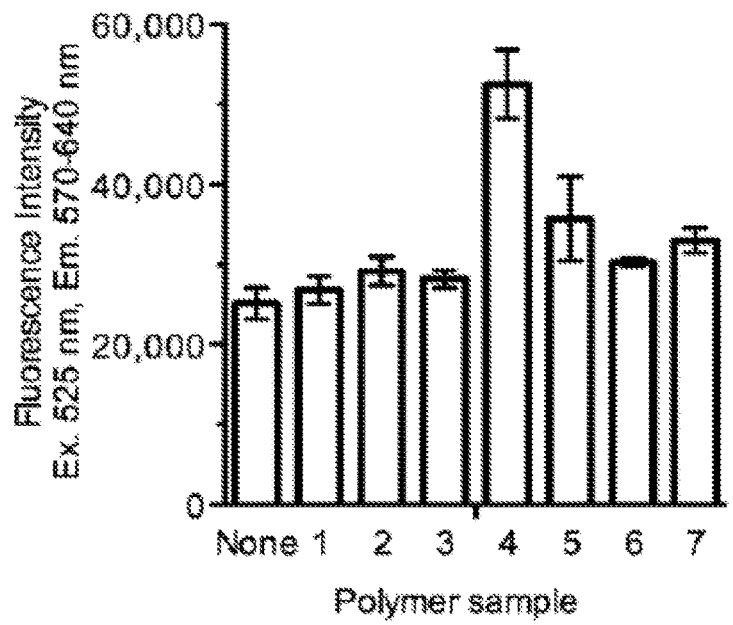
FIG. 16: Analysis of Pd Impurity content in digested polymer samples. 29 μM RAE, 16 ppm polymer, 200 μM TFP, 50 mM NaBH$_4$, 800 mM NH$_4$OAc, EtOH, 24° C., 30 min.

Reaction cocktail described in "General protocol for deallylation of RAE" (1 mL) was added to 2-mL Eppendorf tubes and to each vial was added either 5% TraceMetal $HNO_3$ or polymer suspension in 5% $HNO_3$ (20 μL, [polymer]=16 ppm) and 2.5 M $NaBH_4$ in 10 N NaOH (20 μL). Each solution (200 μL) was transferred to a black 96-well fluorescence plate and the fluorescence (excitation 525 nm, emission 570-640 nm) was measured after 30 min. The result is shown in FIG. 16.

Figure 21A:
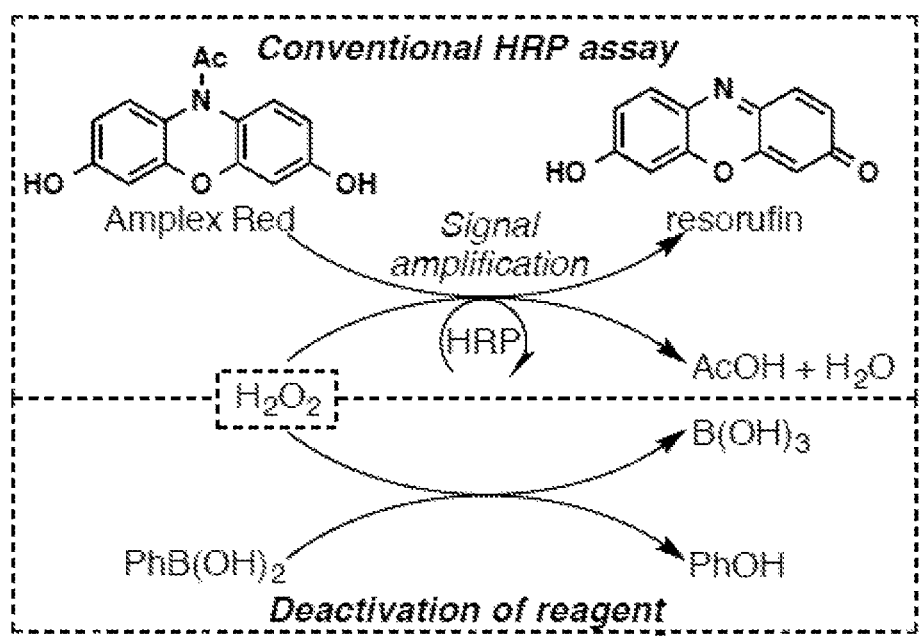
FIGS. 21A-21D: Stop-and-go approach in a horseradish peroxidase system.
Figure 21B:
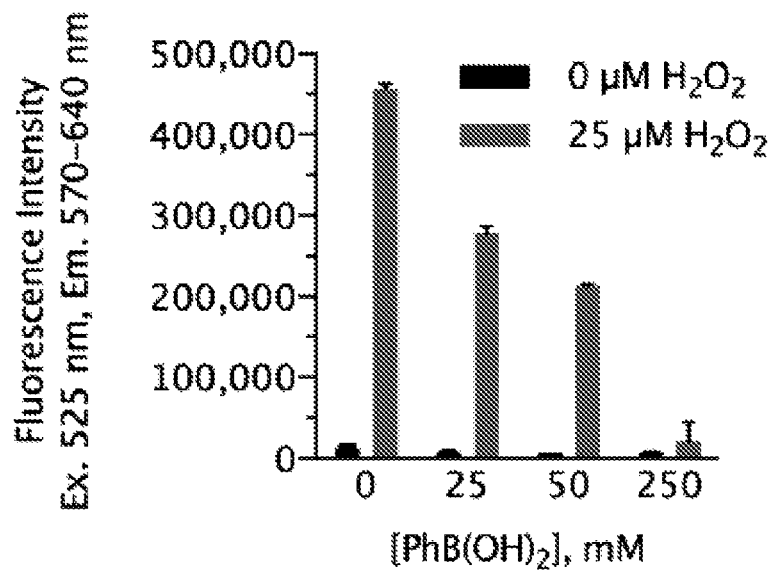

Inhibition of Horseradish Peroxidase:

Amplex Red (a.k.a. Ampliflu Red, 10-acetyl-3,7-dihydroxyphenoxazine) was purchased from Life Technologies (Catalog no. A22188) and was stored at −20° C. in single use ampules as provided. To a scintillation vial was added horseradish peroxidase (3.3 mg 303 U/mg) and 1×PBS (10 mL, 10 U/mL final concentration). The solution was separated into single use 1 mL aliquots and stored at −20° C. To a 2-dram vial was added $PhB(OH)_2$ (15, 30, 150 mg; 0.12, 0.14, 1.2 mmol) and 1×PBS (4.96 mL) to afford stock solutions. To each solution of $PhB(OH)_2$ was added either $H_2O$ or 6.36 mM $H_2O_2$ in $H_2O$ (40 μL) and the solutions were incubated at 24° C. for 10 min. While the solutions were incubating, to a single ampule of Amplex Red (154 μg) was added DMSO (60 μL). The reaction cocktail was prepared by combining 10 mM Amplex Red in DMSO (50 μL), 10 U/mL HRP in 1×PBS (100 μL), and 1×PBS (4.85 mL). Aliquots of the reaction cocktail (50 μL) were transferred to a 96-well black fluorescence plate. To each well was added either 1×PBS with or without 50 μM $H_2O_2$ containing 50, 100, or 500 μM $PhB(OH)_2$. The plate was incubated at 25° C. and fluorescence intensity (excitation 525 nm, emission 570-640 nm) was measured after 30 min. The result is shown in FIG. 21B.

Figure 21C:
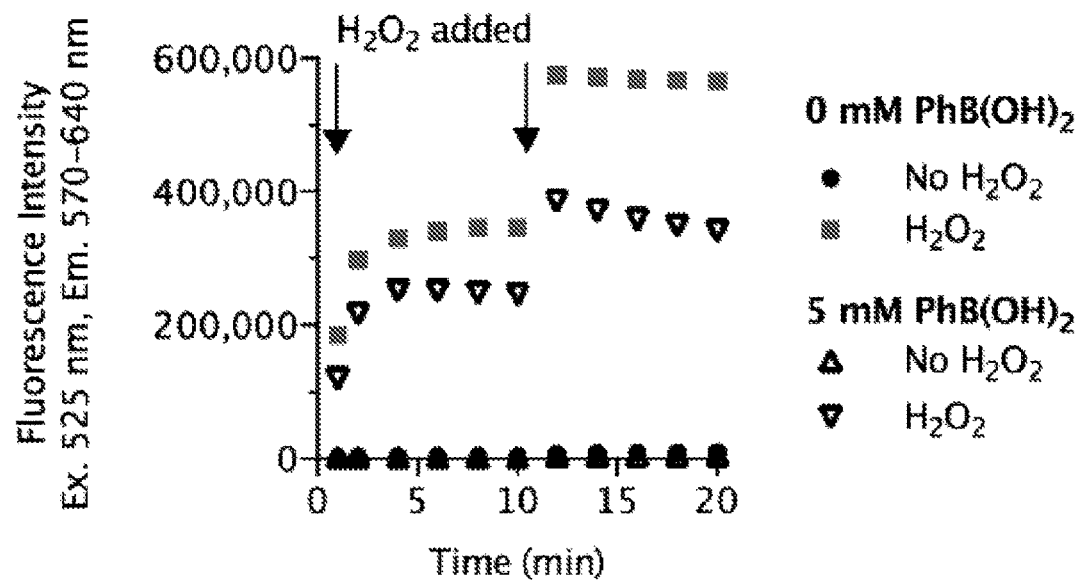

Restarting a Stopped HRP Reaction:

A 20 mM stock solution of $PhB(OH)_2$ was prepared by adding $PhB(OH)_2$ (24 mg, 0.20 mmol) to 1×PBS (10 mL). This solution was divided into aliquots (1.5 mL) and to each was added either $H_2O$ or 1.05 M $H_2O_2$ in $H_2O$ (30 μL). A reaction cocktail was prepared by combining 10 mM Amplex Red in DMSO (25 μL), 10 U/mL horseradish peroxidase (25 μL), and 1×PBS (2.5 mL). Aliquots of the reaction cocktail (50 μL) were transferred to a 96-well black fluorescence plate and to each well was added either 1×PBS with or without 10 μM $H_2O_2$ containing 0 or 10 mM $PhB(OH)_2$ (50 μL). Fluorescence intensity (excitation 525 nm, emission 570-640 nm) was measured every 2 min for 10 min. To each well was again added either 1×PBS with or without 10 μM $H_2O_2$ containing 0 or 10 mM $PhB(OH)_2$ (50 μL). Fluorescence intensity (excitation 525 nm, emission 570-640 nm) was measured every 2 min for 10 min. Data presented in FIG. 21C are normalized to account for the dilution from adding the second aliquot (50 μL) to the solutions on the plate (100 μL) to afford a final volume of 150 μL. Fluorescence intensities are scaled to 1.5× observed values to account for this.

Figure 21D:
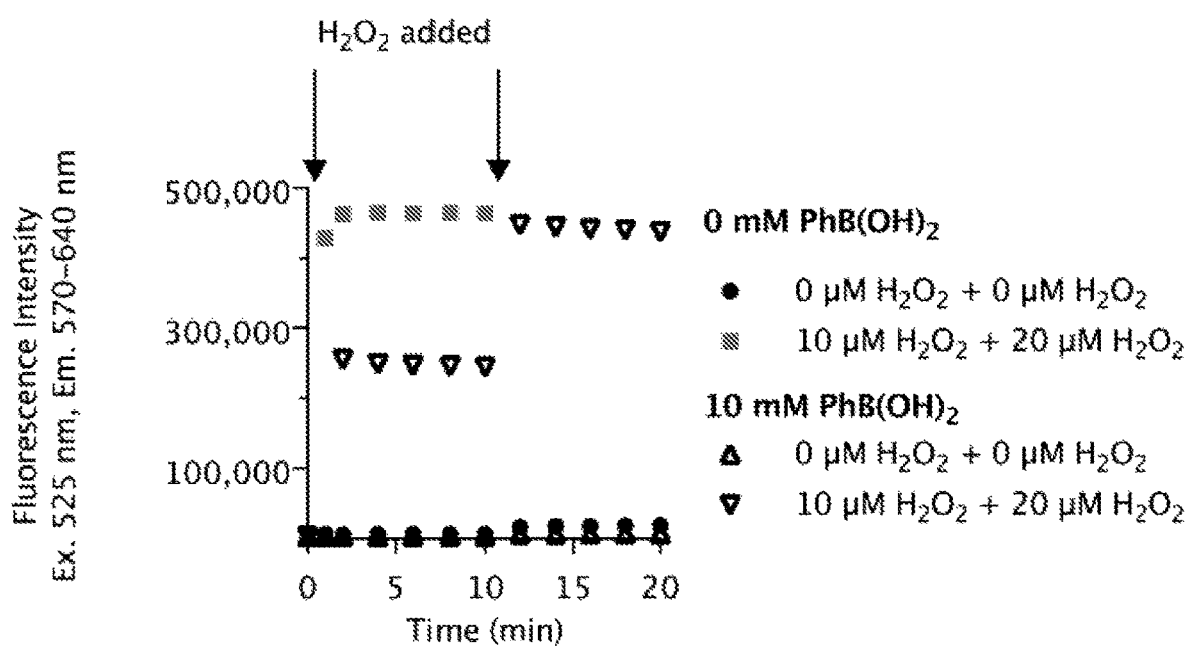

Observed Saturation in Restarting a Stopped HRP Reaction:

A 40 mM stock solution of $PhB(OH)_2$ was prepared by adding $PhB(OH)_2$ (48 mg, 0.40 mmol) to 1×PBS (10 mL). This solution was divided into aliquots (1.5 mL) and to each was added either $H_2O$ or 1.05 M $H_2O_2$ in $H_2O$ (30 μL). A reaction cocktail was prepared by combining 10 mM Amplex Red in DMSO (25 μL), 10 U/mL horseradish peroxidase (250 μL), and 1×PBS (2.25 mL). Aliquots of the reaction cocktail (50 μL) were transferred to a 96-well black fluorescence plate and to each well was added either 1×PBS with or without 10 μM $H_2O_2$ containing 0 or 20 mM $PhB(OH)_2$ (50 μL). Fluorescence intensity (excitation 525 nm, emission 570-640 nm) was measured every 2 min for 10 min. To separate scintillation vials was added 0 or 10 mM $PhB(OH)_2$ in 1×PBS (1.5 mL) and either $H_2O$ (60 μL) or 1.05 M $H_2O_2$ (60 μL), affording new stock solutions. To each well was added the new stock solution, either 1×PBS with or without 20 μM $H_2O_2$ containing 0 or 20 mM $PhB(OH)_2$ (50 μL). Fluorescence intensity (excitation 525 nm, emission 570-640 nm) was measured every 2 min for 10 min. Data presented in FIG. 21D are normalized to account for the dilution from adding the second aliquot (50 μL) to the solutions on the plate (100 μL) to afford a final volume of 150 μL. Fluorescence intensities are scaled to 1.5× observed value to account for this.

Example 2: Demonstration of "Stop-and-Go" Methodology with Colorimetric Palladium Quantification UV-Vis Spectroscopy:

The UV-Vis spectra of RAE and resorufin solutions were acquired using a diode array spectrophotometer (Agilent Technologies, Santa Clara, Calif.) in a quartz cuvette. Other absorbance measurements were recorded in either a 96-well plate using a Modulus II Microplate Multimode reader (Promega, Madison, Wis.) measuring absorbance at 560 nm or in a clear, round bottom 96-well plates on a Spectra Max M5 spectrometer (Molecular Devices, Sunnyvale, Calif.) under the control of a Windows-based PC running software pro V5. The samples were analyzed at λ=580 nm for the resorufin, and at λ=525 nm for RAE.

Fluorescence Measurement:

Fluorescence measurements were read on a Modulus II Microplate Multimode Reader (excitation 525 nm, emission 580-640 nm) or using a HoribaMax Fluorometer (excitation 578 nm, emission 350-700 nm).

Metal Analysis by ICP-MS:

The samples were either diluted or suspended directly in concentrated nitric acid or evaporated with a rotary evaporator first and then re-dissolved in concentrated nitric acid for ICP-MS analysis. Depending on the concentration range of the element, either a Perkin-Elmer Elan 6000 quadrupole ICP-MS spectrometer (Perkin-Elmer, Norwalk, Conn.) or a Thermo Finnigan Element 2 high-resolution ICP-MS spectrometer (Finnigan, Bremen, Germany) was used for the analysis.

General Protocol for Deallylation of RAE:

A reaction cocktail was prepared by mixing 800 mM $NH_4OAc$ in EtOH (10 mL) with 800 μM RAE in EtOH (400 μL) and 3 mM TFP in DMSO, with 250 ppm BHT in DMSO (800 μL). The reaction cocktail (1 mL) was added to individual 2-mL Eppendorf tubes. To half of the samples was added 5% TraceMetal $HNO_3$ (20 μL) as a control. To the other half of the samples was added a $Pd^{2+}$ solution in 5% TraceMetal $HNO_3$ (20 μL). To all samples was added $NaBH_4$ in 10 N NaOH (20 μL). The samples were mixed and transferred (200 μL) to a 96-well black fluorescence well plate. Fluorescence (excitation 525 nm, emission 570-640 nm) was measured every 2 min for 60 min using a Modulus II Microplate Multimode Reader.

Figure 17A:
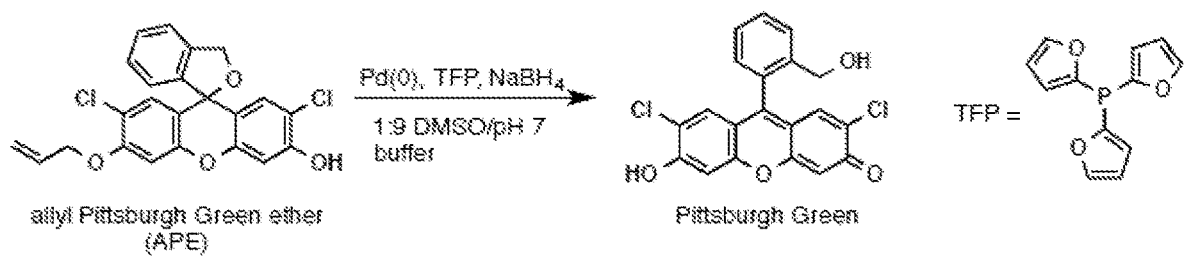
FIGS. 17A-17C.
Figure 17B:
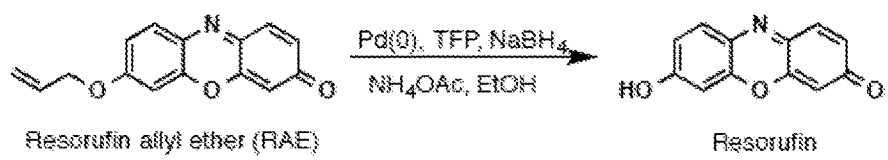
Figure 17C:
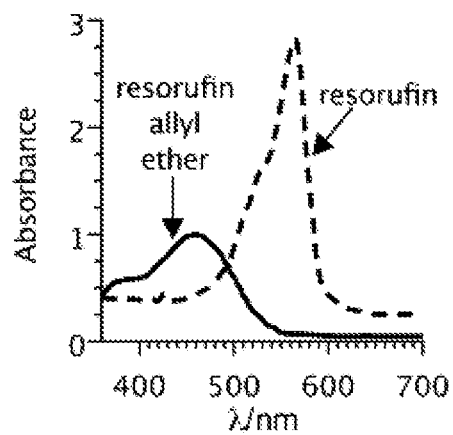

Results and Discussion:

A fluorescence method was described previously for quantifying Pd in pharmaceuticals based on the palladium-catalyzed fluorogenic conversion of allyl Pittsburgh Green ether (APE) to Pittsburgh Green (FIG. 17A). Although that method showed excellent sensitivity and an ability to accurately quantify low-level Pd in real world samples, it was realized that a colorimetric version of the assay could allow even simpler, instrument-free access to low level Pd measurements, a goal previously attempted by several other researchers with limited success. Investigation of a number of candidate chromogenic substrates led to the preparation of yellow-colored resorufin allyl ether (RAE) in one step in 85% yield from commercially available purple-colored resorufin (FIG. 17B). FIG. 17C provides the absorption spectra of resorufin and RAE in 800 mM $NH_4OAc$ in EtOH. Attempts at Pd-catalyzed deallylation of chemosensor RAE using the optimized conditions for APE (tris(2-furyl)phosphine (TFP)), $NaBH_4$, DMSO/1.23 M phosphate pH 7 buffer (1:9)) were unsuccessful. However, screening a variety of commercially available phosphines and additives (FIGS. 2, 3, and 5-7) led to the identification of suitable conditions for carrying out the transformation. Optimized conditions for the Pd-dependent deallylation of RAE employed TFP, $NH_4OAc$ and $NaBH_4$ in an EtOH solvent. Further optimization of RAE as a substrate can be found in Example 1 (Optimization of RAE as a substrate) discussed above.

RAE was found to be selectively responsive to Pd over other metals tested (Ag, Au, Cd, Co, Cr, Fe, Hg, Mn, Ni, Pt, Rh, Ru, Zn, Sr, Ir, Cu) and could detect Pd without interference from these metals, with the exception of Hg, where a small level of interference was observed. When selectivity was tested by absorbance, higher values were observed in the presence of Au, Ag, and Hg due to turbidity of the solution, although fluorescence measurement revealed that these were merely false positives (i.e., these metals did not convert RAE to resorufin; FIGS. 9A-9C). When exposed to Pd, the fluorescence signal increased linearly with respect to Pd concentration, indicating a first-order relationship suitable for convenient quantification.

Figure 18A:
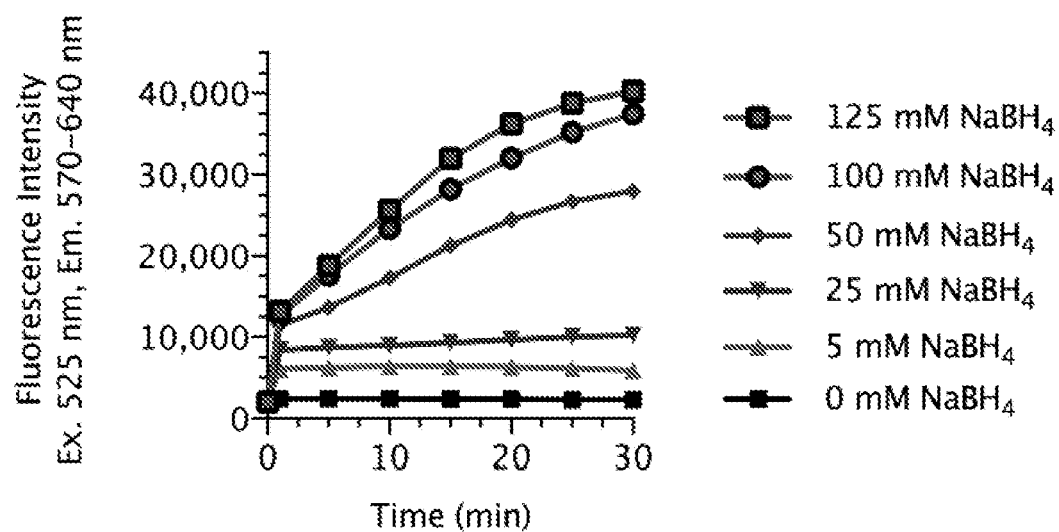
FIGS. 18A-18C: Influence of NaBH$_4$ and NH$_4$OAc on deallylation of RAE.
Figure 18B:
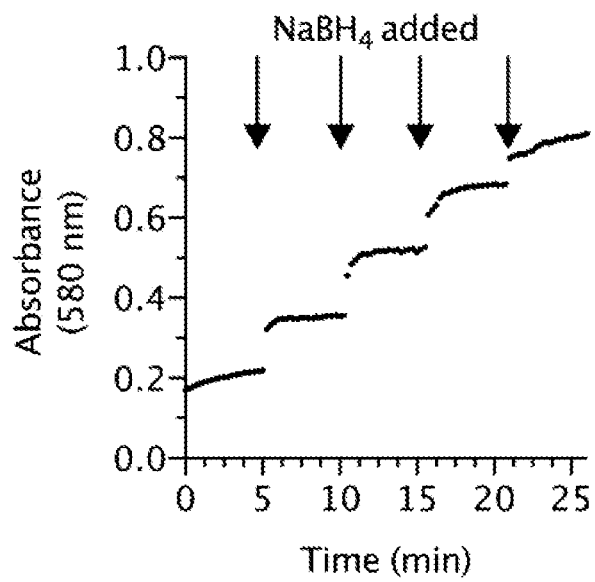

The Pd-catalyzed deallylation of APE in phosphate buffer was more effective in the presence of $NaBH_4$, which reduces Pd(II) and Pd(IV) to catalytically active Pd(0), but did not require this reducing agent as a critical component. In contrast, Pd(II) species did not catalyze the deallylation of RAE in $NH_4OAc$-containing EtOH without the reducing agent, with the amount of $NaBH_4$ dictating the duration of reaction (FIG. 18A). This novel $NaBH_4$-dependence boded well with the aim of competitively and reversibly deactivating catalysis-based assays, as detailed below. Lower concentrations of 5-25 mM $NaBH_4$ led to stalling of the color-forming reaction within 30 seconds, presumably because of rapid consumption of the reductant, $NaBH_4$, combined with ongoing air-oxidation of catalytically active Pd(0) to higher valent, inactive Pd species. In contrast, $NaBH_4$ concentrations in excess of 50 mM allowed the reaction to continue for several minutes. Importantly, the addition of more $NaBH_4$ could restart a stalled deallylation reaction (FIG. 18B), affording a convenient way to trigger signal generation on demand.

Figure 18C:
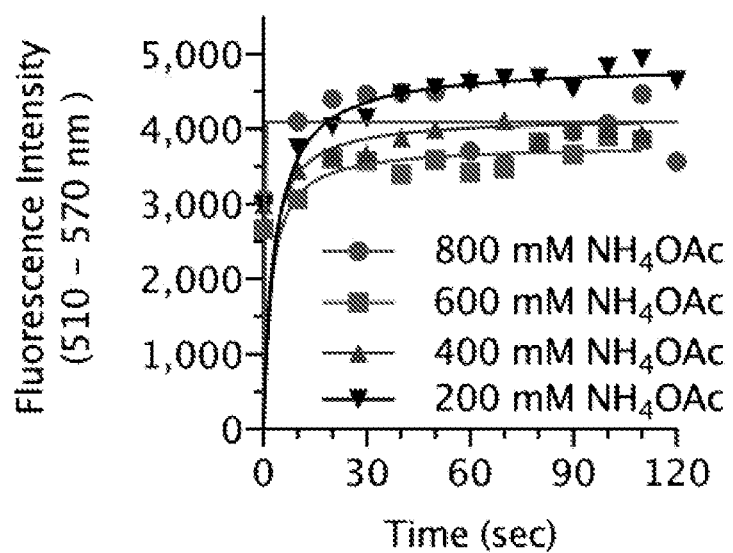

Subsequently, insights into the reaction stalling to rationally expand this developing methodology were sought. The Pd-catalyzed deallylation of APE stalled in the presence of $NH_4OAc$ but continued in a phosphate buffer (FIG. 11). With 200, 400, 600, and 800 mM $NH_4OAC$ followed by pH adjustment, the reactions stalled nearly at the same time (FIG. 18C). The Pd-catalyzed deallylation reaction of RAE under a nitrogen atmosphere was found to stall significantly more slowly than those carried out in open air (FIG. 14), strongly suggesting that aerobic oxidation of Pd(0) to higher order Pd species accounts for the observed reaction stalling. Although lacking critical ligands, (M. M. Konnick, S. S. Stahl, Reaction of molecular oxygen with a PdII-hydride to produce a PdII-hydroperoxide: Experimental evidence for an HX-reductive-elimination pathway. J. Am. Chem. Soc. 130, 5753-5762 (2008)) an acetate-bound Pd species may react with 02 to form a catalytically inactive Pd(II) species that can be reduced by $NaBH_4$ to reform reactive Pd(0).

In an effort to develop a simple, user-friendly colorimetric palladium quantification assay, a reagent cocktail combining all reaction components except $NaBH_4$ was prepared in a single solution. This cocktail, which is stable for over 2 weeks when stored at 5° C., can be dispensed as needed, simplifying application of the colorimetric method. Addition of either 20 μL of a solution or 2-5 mg of a solid sample containing trace Pd to 1 mL of the reaction cocktail, followed by addition of a $NaBH_4$ solution, generated color and fluorescence within 1 min. The color intensity was linearly correlated with Pd concentration, and the dynamic range and reaction time of the assay were tailored by adjusting $NaBH_4$ concentration.

Figure 19A:
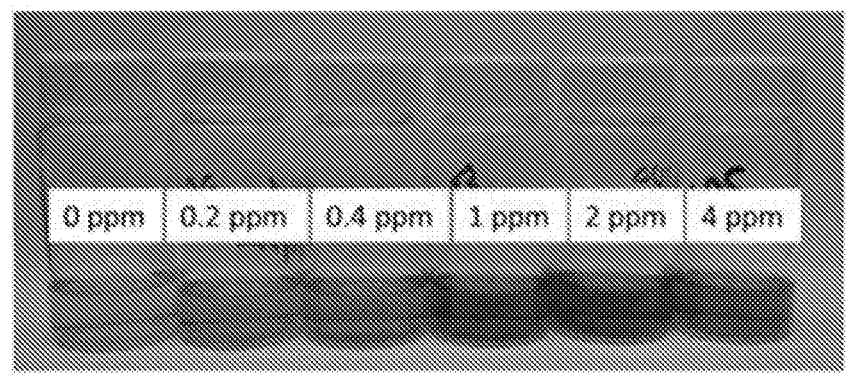
FIGS. 19A-19C: Quantitation of palladium can be performed using either visual examination, measurement of UV-Vis absorbance, or fluorescence with good correlation to ICP-MS.
Figure 19B:
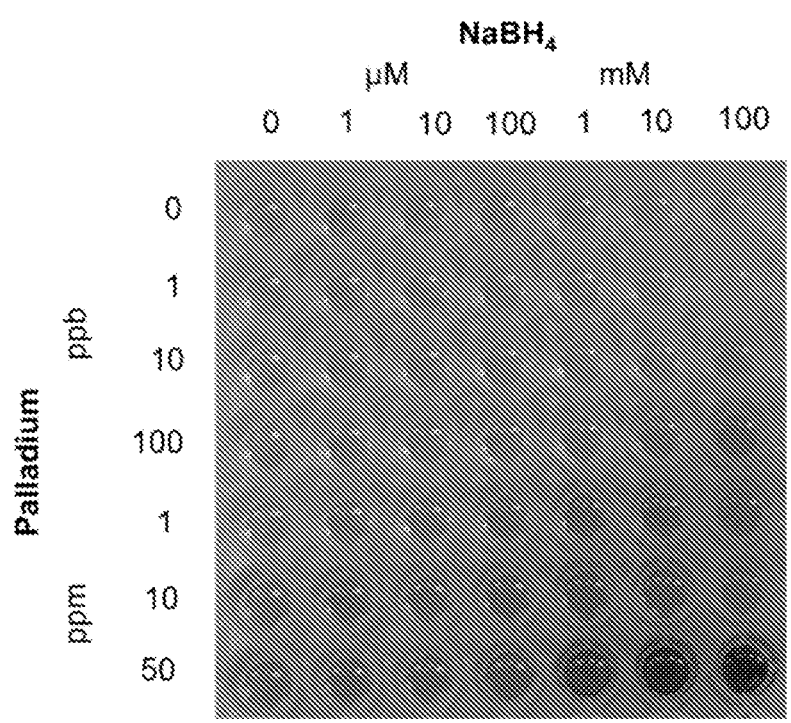
Figure 19C:
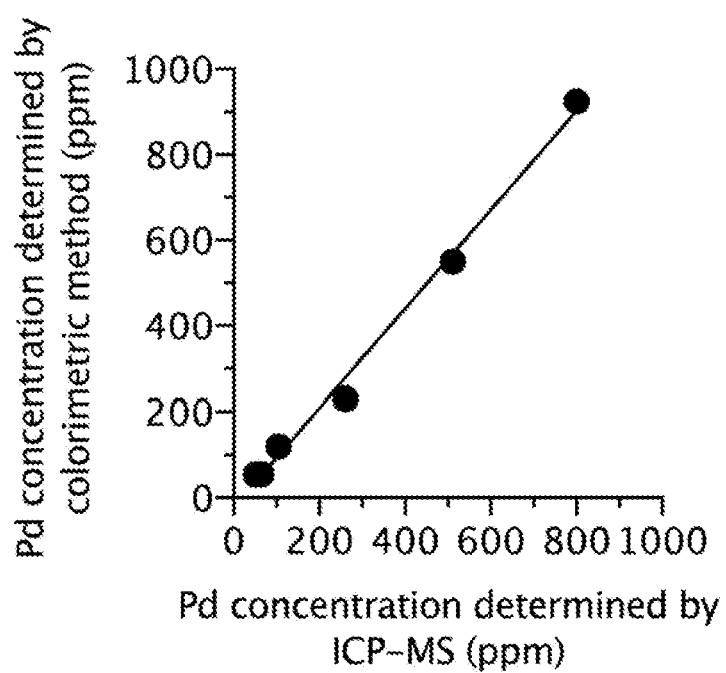

The power of this method is shown in FIGS. 19A-19C. Known concentrations of Pd afford widely different colors with a single concentration of $NaBH_4$, with the color persisting for 24 h (FIG. 19A). If a sample contains 1 ppb palladium, $NaBH_4$ up to 100 mM is required to observe a color change (FIG. 19B). If a sample contains 10 ppm palladium, no $NaBH_4$ is added to observe a color change. Thus, palladium concentrations ranging from 1 ppb to 10 ppm (5 orders of magnitude) can be distinguished in one reaction solution with $NaBH_4$ titration. Alternatively, a user may prepare multiple wells with variable $NaBH_4$ amounts and count a number of colored wells to estimate palladium concentrations.

To confirm that the "stop-and-go" assay approach is providing quantitative data, real-world samples were analyzed. Intermediates used in the preparation of active pharmaceutical ingredients (APIs) were first tested. In pharmaceutical synthesis, reactions may leave behind residual palladium in the products, which is often difficult to remove (K. M. Bullock, M. B. Mitchell, J. F. Toczko, Optimization and scale-up of a Suzuki-Miyaura coupling reaction: development of an efficient palladium removal technique. *Org. Process Res. Dev.* 12, 896-899 (2008)). Various samples were tested from active projects in the Process & Analytical Chemistry department at Merck Research Laboratories in which residual palladium removal has proven difficult. Quantification of palladium was initially performed by ICP-MS followed by analysis using RAE. Compared to the ICP-MS analysis, the stop-and-go approach with RAE provided accuracy from 70 to 120%, with residual palladium concentrations ranging from 62 to 800 ppm (FIG. 19C). These results were satisfactory for this assay approach to be used for screening dozens of routine palladium remediation protocols.

Microscale screening of process adsorbents is often used to identify resins or activated carbons that can be used for selective adsorption of metal impurities in pharmaceutical process research and development (C. J. Welch et al., Adsorbent screening for metal impurity removal in pharmaceutical process research. Org. Process Res. Dev. 9, 198-205 (2005)). Traditionally, this approach requires close coordination with ICP-MS specialists to allow for quick turnaround time. However, often because of instrument calibration, the vast number of samples, and preparation time, this can be time consuming. As such, the pharmaceutical industry has been interested in a faster technology for trace metal analysis (Thayer, A. M., Trace metals debate. *Chem. Eng. News* 91(33):10-13 (2013)).

Figure 20:
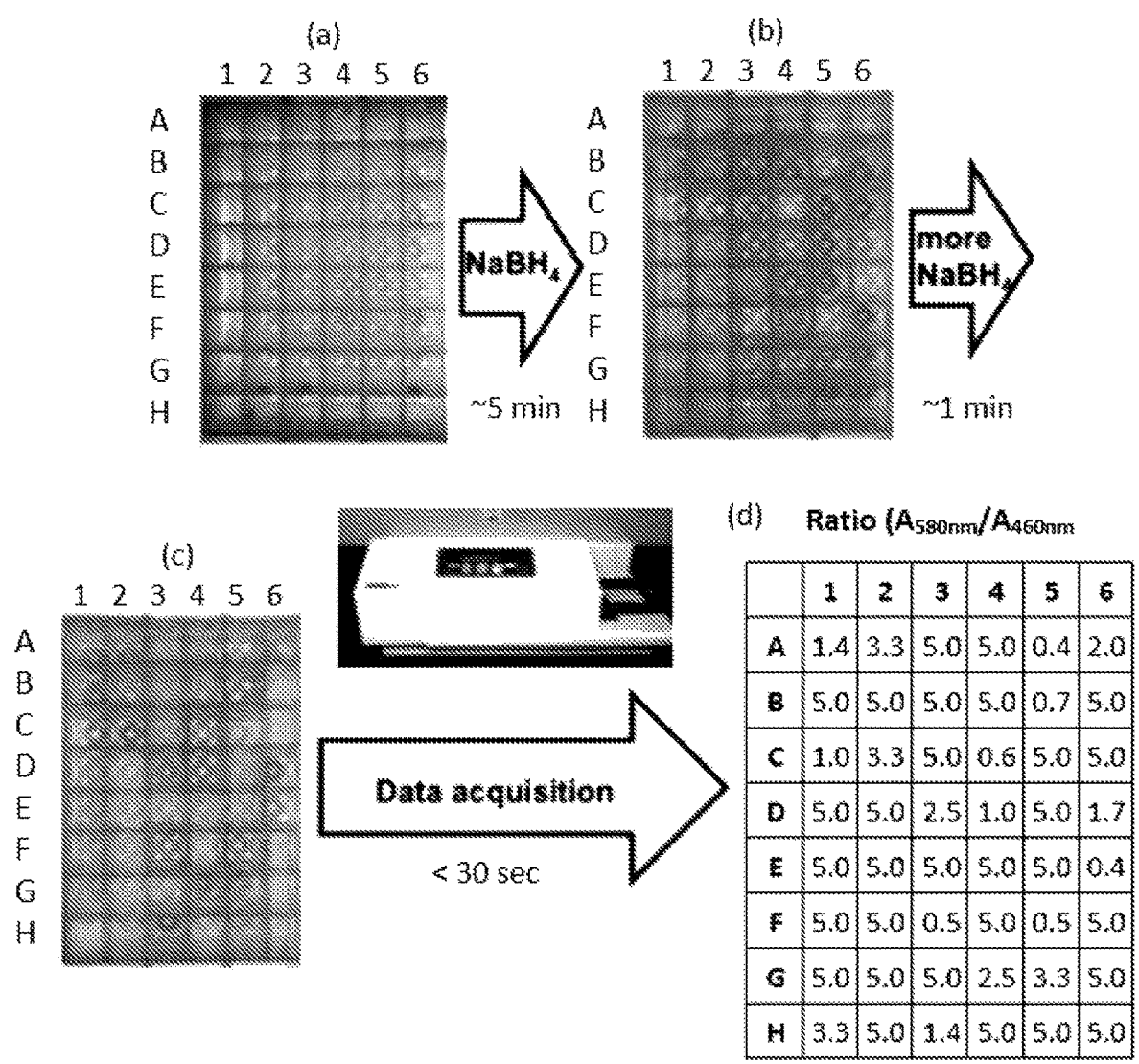
FIG. 20: Case study a streamlined process combining adsorbent screening for Pd removal with high-throughput colorimetric Pd detection.

The application of the colorimetric method enables rapid determination of palladium concentrations 'on the spot', in the same laboratory where the process development studies are being carried out. FIG. 20 shows the results of a high throughput screen of Pd impurity remediation treatments of a pharmaceutical intermediate with 48 metal-scavenging adsorbents, using the stop and go assay with RAE to visualize relative Pd levels. An aliquot from each well is treated with the reaction cocktail (FIG. 20, panel (a)), then with $NaBH_4$. In less than 5 min, gross differences in palladium concentration are readily apparent to the naked eye by distinguishable colors (FIG. 20, panel (b)). At this point, the reaction had stalled, and too many hits were identified. Accordingly, more $NaBH_4$ was added to restart the reaction, accentuating the differences between wells and enabling rapid determination of the potential most effective treatments for residual Pd remediation (FIG. 20, panel (c)). A high-throughput mapping of relative palladium concentration was obtained by plotting the ratio of absorbance at 580 and 460 nm using a UV-Vis plate reader (read time for 48 samples <30 sec) (FIG. 20, panel (d)). These results quantitatively confirm the most effective palladium removal treatments to be wells A5, E6, F3, and F6. Spot-checking several adsorbent treatment samples using conventional ICP-MS showed a good correlation with the colorimetric method, with the selection of the most effective adsorbent treatments (A5, E6) being identical in both cases. These results demonstrate the utility of a stop-and-go approach in trace metal quantification, providing an important advance for process chemists dealing with remediation of palladium impurity problems using 'point-of-use' high-throughput analysis.

APE was previously used for quantifying palladium in ore samples without requiring acidic sample digestion (J. M. Williams, et al., A high-throughput method to detect palladium in ores. *Ind. Eng. Chem. Res.* 52:8612-8615 (2013)), a significant improvement over standard analytical methods such as ICP-MS, but still requiring the use of a blue light source to check fluorescence intensity. This requirement associated with the fluorometric method was not ideal for turbid samples such as ores. Therefore, the described colorimetric method was applied for more convenient visualization. It was found that the reaction was stalled prior to effective Pd extraction from the ores, leading to a need to add a large excess of $NaBH_4$. However, a 1 min pre-incubation in a DMSO solution of TFP with sonication, followed by the addition of RAE, $NH_4OAc$, EtOH and $NaBH_4$ afforded subpar semi-quantitative data. A second addition of $NaBH_4$ after the reaction had stalled provided good colorimetric agreement with previous semi-quantitative analysis (J. M. Williams, K. Koide, A high-throughput method to detect palladium in ores. *Ind. Eng. Chem. Res.* 52, 8612-8615 (2013)) (FIG. 15) within 20 min. Similarly, we were able to detect Pd in polymer samples prepared by Pd catalysis. A digestion protocol analogous to the ore samples was employed, affording semi-quantitative data regarding trace amounts of Pd (see Example 1 "Optimization of RAE as a substrate" above).

Example 3: Demonstration of Competitive and Reversible Deactivation Using Enzymatic Catalysis with Horseradish Peroxidase (HRP)

Materials and Methods:
UV-Vis Spectroscopy:
The UV-Vis spectra of RAE and resorufin solutions were acquired using a diode array spectrophotometer (Agilent Technologies, Santa Clara, Calif.) in a quartz cuvette. Other absorbance measurements were recorded in either a 96-well plate using a Modulus II Microplate Multimode reader (Promega, Madison, Wis.) measuring absorbance at 560 nm or in a clear, round bottom 96-well plates on a Spectra Max M5 spectrometer (Molecular Devices, Sunnyvale, Calif.) under the control of a Windows-based PC running software pro V5. The samples were analyzed at $\lambda=580$ nm for the resorufin, and at $\lambda=525$ nm for RAE.

Fluorescence Measurement:
Fluorescence measurements were read on a Modulus II Microplate multimode Reader (excitation 525 nm, emission 580-640 nm) or using a HoribaMax Fluorometer (excitation 578 nm, emission 350-700 nm).

Metal Analysis by ICP-MS:
The samples were either diluted or suspended directly in concentrated nitric acid or evaporated with a rotary evaporator first and then re-dissolved in concentrated nitric acid for ICP-MS analysis. Depending on the concentration range of the element, either a Perkin-Elmer Elan 6000 quadrupole ICP-MS spectrometer (Perkin-Elmer, Norwalk, Conn.) or a Thermo Finnigan Element 2 high-resolution ICP-MS spectrometer (Finnigan, Bremen, Germany) was used for the analysis.

General Protocol for Deallylation of RAE:
A reaction cocktail was prepared by mixing 800 mM $NH_4OAc$ in EtOH (10 mL) with 800 µM RAE in EtOH (400 µL) and 3 mM TFP in DMSO, with 250 ppm BHT in DMSO (800 µL). The reaction cocktail (1 mL) was added to individual 2-mL Eppendorf tubes. To half of the samples was added 5% TraceMetal $HNO_3$ (20 µL) as a control. To the other half of the samples was added a $Pd^{2+}$ solution in 5% TraceMetal $HNO_3$ (20 µL). To all samples was added $NaBH_4$ in 10 N NaOH (20 µL). The samples were mixed and transferred (200 µL) to a 96-well black fluorescence well plate. Fluorescence (excitation 525 nm, emission 570-640 nm) was measured every 2 min for 60 min using a Modulus II Microplate Multimode Reader.

Results and Discussion:

Horseradish peroxidase (HRP) is a common enzyme for detection and quantification in biological assays. This enzyme catalytically converts Amplex Red (10-acetyl-3,7-dihydroxyphenoxazine) and $H_2O_2$ to resorufin, acetic acid, and $H_2O$. (FIG. 21A). The reaction continues indefinitely until either Amplex Red or $H_2O_2$ is consumed, at which point, signal generation is stopped.

To illustrate the discontinuous catalysis approach in a different assay, a system was designed in which $PhB(OH)_2$ would competitively reduce $H_2O_2$ (FIG. 21A "Deactivation of reagent") while the $H_2O_2$-mediated oxidation of Amplex Red occurs ("Conventional HRP assay"). FIG. 21B shows that $PhB(OH)_2$ was able to do so in a concentration-dependent manner, affording lower signals. Reactions halted by consumption of $H_2O_2$ could be restarted by an addition of a fresh aliquot of $H_2O_2$ (FIG. 21C). With a further addition of $H_2O_2$, signal saturation occurred (FIG. 21D). With the inclusion of the competitive scavenger, $PhB(OH)_2$ to remove $H_2O_2$ from the system, the discontinuous catalysis alleviated the problem of overshooting signals as well as allowed us to restart the reaction without problematic increases in fluorescence (FIG. 21D). Although the protocol has not been fully optimized in an HRP system, these data indicate a great potential for the applications of discontinuous catalysis in other enzyme assays.

In conclusion, a competitive and reversible deactivation approach for catalytic quantification assays was developed. Conversion of RAE to resorufin via a Pd-catalyzed Tsuji-Trost reaction is autonomously stalled by the oxidation of reactive Pd(0) to non-reactive species. Addition of $NaBH_4$ as a reducing agent is able to restart the reaction, enabling accurate measurements over 5 orders of magnitude. Notably, even in cases where the amount of Pd far exceeds the amount of RAE, the data remain quantitative. The utility of the same concept was demonstrated in a widely-used HRP assay system, where competitive destruction of $H_2O_2$ by $PhB(OH)_2$ leads to reaction stalling, broadening the dynamic range of the assay. These approaches should be compatible with automation and may find further applicable arenas to broaden the dynamic ranges of catalysis-based assays.

Having described this invention, it will be understood to those of ordinary skill in the art that the same can be performed within a wide and equivalent range of conditions, formulations and other parameters without affecting the scope of the invention or any embodiment thereof.

We claim:

1. A method of detecting an analyte in a test sample, comprising:
    conducting a catalytic reaction under an oxygen-containing environment that produces a detectable product in the presence of an analyte in a reaction mixture in the presence of an inactivator of the reaction, wherein the inactivator depletes a limiting component of the reaction, thereby stalling the reaction, wherein the analyte is Pd;
    adding a restorative composition to the reaction mixture after the reaction has stalled, thereby restoring the depleted limiting component to restart the reaction one or more times, wherein the inactivator depletes the restored limiting component of the reaction thereby again stalling the reaction; and
    detecting the presence of the detectable product of the catalytic reaction in the reaction mixture,
    where the reaction mixture comprises resorufin allyl ether (RAE) and $NH_4OAc$ in ethanol and the restorative composition comprises $NaBH_4$.

2. The method of claim 1, wherein the limiting component is a catalyst of the catalytic reaction.

3. The method of claim 1, comprising quantifying the presence of the detectable product of the catalytic reaction in the reaction mixture.

4. The method of claim 1, wherein the limiting component is depleted by oxidation and is restored by addition of a reducing agent.

5. The method of claim 1, wherein the limiting component is depleted by oxidation in the presence of oxygen.

6. The method of claim 2, in which the reaction is conducted in a multi-well plate, with at least two wells comprising different amounts of $NaBH_4$.

7. The method of claim 1, wherein the oxygen-containing environment comprises oxygen, an oxygen-containing gas mixture, or air.

8. A method of detecting an analyte in a test sample, comprising:
    conducting a catalytic reaction that produces a detectable product in the presence of an analyte in a reaction mixture in the presence of an inactivator of the reaction, wherein the inactivator depletes a limiting component of the reaction, thereby stalling the reaction;
    adding a restorative composition to the reaction mixture after the reaction has stalled, thereby restoring the depleted limiting component to restart the reaction one or more times, wherein the inactivator depletes the restored limiting component of the reaction thereby again stalling the reaction; and
    detecting the presence of the detectable product of the catalytic reaction in the reaction mixture;
    wherein the reaction is catalyzed by an enzyme, and the limiting component is a substrate of the enzyme.

9. The method of claim 8, wherein the enzyme is a peroxidase, and the limiting component is $H_2O_2$.

10. The method of claim 9, wherein the inactivator is a boronic acid.

11. The method of claim 10, wherein the boronic acid is phenylboronic acid.

12. The method of claim 8, in which the reaction is a HRP-detection reaction, the limiting component is $H_2O_2$, the inactivator is $PhB(OH)_2$, and the restorative composition comprises $H_2O_2$.

13. The method of claim 8, comprising quantifying the presence of the detectable product of the catalytic reaction in the reaction mixture.

14. The method of claim 8, wherein the limiting component is depleted by oxidation and is restored by the addition of a reducing agent.

15. The method claim 8, wherein the limiting component is depleted by oxidation in the presence of oxygen.

16. The method of claim 9, in which the reaction is conducted in a multi-well plate, with at least two wells comprising different amounts of $H_2O_2$.

* * * * *

UNITED STATES PATENT AND TRADEMARK OFFICE
CERTIFICATE OF CORRECTION

PATENT NO. : 11,220,703 B2
APPLICATION NO. : 15/778855
DATED : January 11, 2022
INVENTOR(S) : Xiaodong Bu et al.

Page 1 of 1

It is certified that error appears in the above-identified patent and that said Letters Patent is hereby corrected as shown below:

In the Claims

Column 22, Line 58, Claim 15, delete "method" and insert -- method of --

Signed and Sealed this
Fifteenth Day of March, 2022

Drew Hirshfeld
*Performing the Functions and Duties of the*
*Under Secretary of Commerce for Intellectual Property and*
*Director of the United States Patent and Trademark Office*